US008012328B2

(12) United States Patent
Henry et al.

(10) Patent No.: US 8,012,328 B2
(45) Date of Patent: Sep. 6, 2011

(54) NON-FLUIDIC MICRO-DETECTION DEVICE AND USES THEREOF

(75) Inventors: Charles S. Henry, Fort Collins, CO (US); Carlos D. Garcia, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 1394 days.

(21) Appl. No.: 10/568,975

(22) PCT Filed: Jul. 8, 2004

(86) PCT No.: PCT/US2004/021740
§ 371 (c)(1),
(2), (4) Date: Sep. 12, 2006

(87) PCT Pub. No.: WO2005/024408
PCT Pub. Date: Mar. 17, 2005

(65) Prior Publication Data
US 2007/0039822 A1    Feb. 22, 2007

Related U.S. Application Data

(60) Provisional application No. 60/496,673, filed on Aug. 21, 2003.

(51) Int. Cl.
*C25B 11/02* (2006.01)
*G01N 27/26* (2006.01)
(52) U.S. Cl. .................................... 204/603; 204/230.1
(58) Field of Classification Search .............. 204/403.01, 204/230.1, 603
See application file for complete search history.

(56) References Cited

U.S. PATENT DOCUMENTS

| 6,045,676 A | 4/2000 | Mathies et al. |
| 6,103,199 A | 8/2000 | Bjornson et al. |
| 6,159,353 A | 12/2000 | West et al. |
| 6,274,089 B1 | 8/2001 | Chow et al. |
| 2008/0135410 A1* | 6/2008 | Henry et al. ............ 204/450 |

FOREIGN PATENT DOCUMENTS

| WO | WO 00/75650 A1 | 12/2000 |
| WO | WO 01/06228 A2 | 1/2001 |

OTHER PUBLICATIONS

Martin, R.S., et al. "In-channel electrochemical detection for microchip capillary electrophoresis using an electrically isolated potentiostat", Analytical Chemistry, vol. 74, No. 5, Mar. 1, 2002, p. 1136-1143.*
Blaedel, W.J., Flow Electrolysis on a Reticulated Vitreous Carbon Electrode, Analytical Chemistry, vol. 51, No. 7, (Jun. 7, 1979), pp. 799-802.

(Continued)

*Primary Examiner* — Jeffrey T Barton
*Assistant Examiner* — J. Christopher Ball
(74) *Attorney, Agent, or Firm* — Katten Muchin Roseman, LLP

(57) ABSTRACT

The present invention provides a microchip for performing electrophoresis with pulsed amperometric detection (PAD) for the separation and detection of underivatized carbohydrates, amino acids, sulfur-containing antibiotics, etc. PAD allows for the direct detection of amines, thiols, alcohols and carbohydrates and therefore is a useful technique for the development of electrochemical detection for microchip electrophoresis.

55 Claims, 16 Drawing Sheets

OTHER PUBLICATIONS

Galloway, M., et al., Contact Conductivity Detection in Poly(methylmethacrylate)-Based Microfluidic Devices for Analysis of Mono- and Polyanionic Molecules, vol. 74 No. 10 (May 15, 2002), pp. 2407-2415.

Kurita, R., et al., Microfluidic device integrated with pre-reactor and dual enzyme-modified microelectrodes for monitoring in vivo glucose and lactate, (2002), pp. 296-303.

Deng, T., et al. Fabrication of Metallic Microstructures Using Exposed, Developed Silver Halide-Based Photographic Film, Analytical Chemistry, vol. 72, No. 4, (Feb. 15, 2000), pp. 645-651.

Stevens, N.P., et al. Steady-State Voltammetry Using Microwire Electrodes under Microfluidic Control, J. Phys. Chem. (2000), pp. 7110-7114.

Booth, J., et al., Hydrodynamic Voltammetry with Channel Electrodes: Microdisc Electrodes, J. Phys. Chem. (1995), pp. 10942-10947.

Blaedel, W.J., et al., Submicromolar Concentration Measuremetns with Tubular Electrodes, Analytical Chemistry, vol. 43, No. 12 (Oct. 12, 1971), pp. 1538-1540.

Compton, R.G., et al., Hydrodynamic Voltammetry with Microelectrodes. Channel Electrodes: Theory and Experiment, J. Phys. Chem. (1993), pp. 10410-10415.

International Search Report mailed Dec. 23, 2004 for PCT/US2004/021740.

Auroux, P.A., Iossifidis, D., Reyes, D. R., Manz, A., Anal. Chem. 2002, 74, 2637-2652.

Becker, H., Locascio, L., Talanta 2002. 56, 267-287.

Casella, I.G., Contursi, M., Desimoni, E., Analyst 2002, 127, 647-652.

Chiari, M., Cretich, M., Consonni, R., Electrophoresis 2002, 23, 536-541.

Deore, B., Yakabe, H., Shiigi, H., Nagaoka, T., Analyst 2002, 127, 935-939.

Dolnik, V., Liu, S. Jovanovich, S., Electrophoresis 2000, 21, 41-54.

Duffy, D.C., McDonald, J.C., Schueller, O. J. A., Whitesides, G.M., Anal. Chem. 1998, 70, 4974-4984.

Fanguy, J.C., Henry, C.S., Analyst 2002, 127, 1021-1023; Garcia, G., Garcia, C.D., Oritz, P.I., DePauli, C.P., J. Electronanal. Chem. 2002, 519, 53-59.

Ferrance, J., Landers, J.P., Luminescence 2001, 16, 79-88.

Ferrance, J., Snow, K., Landers, J.P., Clin. Chem. 2002, 48, 380-383.

Garcia, C.D., Hadley, D.G., W.W., W., Henry, C.S., Biotechnol. Prog. 2003.

Garcia, C.D., Oritz, P.I., Electroanalysis 2000, 12, 1074-1076.

Garcia, G., Garcia, C.D., Oritz, P.I., De Pauli, C.P., J. Electroanal. Chem. 2002, 519, 53-59.

Garcia, C.D., Oritz, P.I., Electroanalysis 1998, 10, 832-835.

Guijt, R.M., Baltussen, E., van Dedem, G.W., Electrophoresis 2002, 23, 823-835.

Hu, Q., Zhou, T., Hu, G., Fang, Y., J. Pharm. Biomed. Anal. 2002, 30, 1047-1053.

Hughes, S., Johnson, D.C., Anal. Chim. Acta 1981, 132, 11-22.

Johnson, D.C., Dobberpuhl, D., Roberts, R., Vandeberg, P., J. Chromatogr. 1993, 640, 79-96.

Lacher, N.A., Garrison, K.E., Martin, R.S., Lunte, S.M., Electrophoresis 2001, 22, 2526-2536.

LaCourse, W.R., Pulsed Electrochemical Detection in High-Performance Liquid Chromatography; Wiley J. & Sons: New York, 1997.

LaCourse, W.R., Johnson, D.C., Rey, M.A., Slingsby, R.W., Anal. Chem. 1991, 63, 134-139.

Lacher, N.A., Garrison, K.E., Martin, R.S., Lunte, S.M., Electrophoresis 2001, 22, 2526-2536.

Linder, V., Verpoorte, E., de Rooij, N.F., Sigrist, H., Thormann, W., Electrophoresis 2002, 23, 740-749.

Lu, W., Cassidy, R., Anal. Chem. 1993, 65, 2878-2881.

Manica, D.P., Ewing, A.G., Electrophoresis 2002, 23, 3735-3743.

Martin, R.S., Gawron, A.J., Lunte, S.M., Henry, C.S., Analytical Chemistry 2000, 72, 3196-3202.

Ng. J.M., Gitlin, I., Stroock, A.D., Whitesides, G.M., Electrophoresis 2002, 23, 3461-3473.

Owens, G.S., LaCourse, W.R., J. Chromatogr., B 1997, 695, 15-25.

O'Shea, T.J., Lunte, S.M., LaCourse, W.R., Anal. Chem. 1993, 65, 948-867.

Reyes, D.R., Iossifidis, D., Auroux, P.A., Manz, A., Anal. Chem. 2002, 74, 2623-2636.

Rossier, J., Reymond, F., Michel, P.E., Electrophoresis 2002, 23, 858-867.

Schwartz, M.A., Galliker, B., Fluri, K., Kappes, T., Hauser, P.C., Analyst 2001, 126, 147-151.

Soga, T., Inoue, Y., J. Chromatogr. 1993, 620, 175-181; and Takizawa, K., Nakamura, H., Anal. Sci. 1998, 14, 925-928.

Springer Verlag, 2000; and Casella, I.G., Contursi, M., Desimoni, E., Analyst 2002, 127, 647-652.

Stefansson, M., Westerlund, D., J. Chromatogr. 1993, 632, 195-200.

Terry, S.C., Jerman, J.H., Angell, J.B., IEEE Trans. Electron. Devices 1979, ED-26, 1880.

Takizawa, K., Nakamura, H; Analytical Sciences; 1998, vol. 14; 925-928.

Vandaveer, W.R., IV, Pasas, S.A., Martin, R.S., Lunte, S.M., Electrophoresis 2002, 23, 3667-3677.

Verpoorte, E. Electrophoresis 2002, 23, 677-712.

Wang, J., Talanta 2002, 56, 223-231.

Wang, J., Trends in Anal. Chem. 2002, 21, 226-232.

Weigl, B.H., Bardell, R.L., Cabrera, C.R., Adv. Drug. Deliv. Rev. 2003, 55, 349-377.

Wen, J., Cassidy, R.M., Baranski, A.S., J. Chromatogr., A 1998, 811, 181-192.

Zhang, L., Dang, F., Baba, Y., J. Pharm. Biomed. Anal. 2003, 30, 1645-1654.

\* cited by examiner

FIG. 3

|  | Carbohydrates | Amino Acids | Antibiotics |
|---|---|---|---|
| Clean | +1.4 V | +1.8 V | +1.8 V |
| Reactivate | -0.5 V | -0.5 V | -0.5 V |
| Detect | +0.7 V | +0.7 V | +0.5 V |

FIG. 4

| Reservoir | Containing | Injection / V | Separation / V |
|---|---|---|---|
| A | Buffer | + 410 | + 1000 or + 1700 |
| B | Buffer | - 160 | + 410 |
| C | Sample | + 410 | + 410 |
| D | Waste | Ground | Ground |

NON-FLUIDIC MICRO-DETECTION DEVICE AND USES THEREOF

CROSS-REFERENCE TO RELATED APPLICATIONS

This application is a national stage application and claims the priority of PCT/US2004/021740, filed on Jul. 8, 2004, which claims the priority of U.S. Provisional Application No. 60/496,673, filed on Aug. 21, 2003. The entire disclosure and contents of the above patents and applications are hereby incorporated by reference.

BACKGROUND

1. Field of the Invention

The present invention relates generally to electrophoresis, and more particularly to a microchip that performs electrophoresis, a method to produce a microchip with integrated electrodes, and a method for performing electrophoresis using a microchip with integrated electrodes.

2. Related Art

Microanalytical devices open up new possibilities for the miniaturization of conventional chemical and biochemical analysis systems. Since the introduction of the Miniaturized Total Analysis System (μTAS) less than 15 years ago, an enormous number of papers have been published showing the capabilities of these devices, see Terry, S. C., Jerman, J. H., Angell, J. B., IEEE Trans. Electron. Devices 1979, ED-26, 1880; Verpoorte, E. Electrophoresis 2002, 23, 677-712; Reyes, D. R., Iossifidis, D., Auroux, P. A., Manz, A., Anal. Chem. 2002, 74, 2623-2636; Auroux, P. A., Iossifidis, D., Reyes, D. R., Manz, A., Anal. Chem. 2002, 74, 2637-2652, the entire contents and disclosures of which are hereby incorporated by reference. Some of the advantages of the μTAS over conventional bench-top systems include custom design, reduced consumption of reagents and sample, lower waste generation and increased analysis speed and portability, see Ng, J. M., Gitlin, I., Stroock, A. D., Whitesides, G. M., Electrophoresis 2002, 23, 3461-3473, the entire contents and disclosure of which is hereby incorporated by reference. Born as the combination of microelectronics technology and capillary electrophoresis, microanalytical devices were initially constructed using silicon or glass substrates. A wide variety of polymeric materials have been used more recently, see Becker, H., Locascio, L., Talanta 2002, 56, 267-287, the entire contents and disclosure of which is hereby incorporated by reference. In particular, poly(dimethylsiloxane) (PDMS) has been used extensively because it is robust, optically transparent, non-polar, impermeable to aqueous solutions and allows the easy, fast, and inexpensive fabrication of devices by using micromolding techniques, see Duffy, D. C., McDonald, J. C., Schueller, O. J. A., Whitesides, G. M., Anal. Chem. 1998, 70, 4974-4984, the entire contents and disclosure of which is hereby incorporated by reference. Although there are some examples of pressure-driven applications, PDMS has been used extensively for microchip electrophoresis with a variety of applications including immunoanalysis, DNA analysis, and small molecule determinations, see Reyes, D. R., Iossifidis, D., Auroux, P. A., Manz, A., Anal. Chem. 2002, 74, 2623-2636; Auroux, P. A., Iossifidis, D., Reyes, D. R., Manz, A., Anal. Chem. 2002, 74, 2637-2652; Garcia, C. D., Hadley, D. G., W. W., W., Henry, C. S., Biotechnol. Prog. 2003, in press; Guijt, R. M., Baltussen, E., van Dedem, G. W., Electrophoresis 2002, 23, 823-835; Linder, V., Verpoorte, E., de Rooij, N. F., Sigrist, H., Thormann, W., Electrophoresis 2002, 23, 740-749; Weigl, B. H., Bardell, R. L., Cabrera, C. R., Adv. Drug. Deliv. Rev. 2003, 55, 349-377; Zhang, L., Dang, F., Baba, Y., J. Pharm. Biomed. Anal. 2003, 30, 1645-1654; Chiari, M., Cretich, M., Consonni, R., Electrophoresis 2002, 23, 536-541; Dolnik, V., Liu, S., Jovanovich, S., Electrophoresis 2000, 21, 41-54; Manica, D. P., Ewing, A. G., Electrophoresis 2002, 23, 3735-3743; Wang, J., Talanta 2002, 56, 223-231; and Rossier, J., Reymond, F., Michel, P. E., Electrophoresis 2002, 23, 858-867, the entire contents and disclosures of which are hereby incorporated by reference.

Many modes of detection have been employed to monitor separations on microanalytical devices but the most used detection method is laser induced fluorescence (LIF), see Ferrance, J., Landers, J. P., Luminescence 2001, 16, 79-88; and Ferrance, J., Snow, K., Landers, J. P., Clin. Chem. 2002, 48, 380-383, the entire contents and disclosures of which are hereby incorporated by reference. However, the cost of optical instrumentation, the need for analyte derivatization, and the limited portability of LIF has led to the investigation of electrochemical detection (ECD), an attractive alternative for microchip devices, see Verpoorte, E., Electrophoresis 2002, 23, 677-712; Wang, J., Talanta 2002, 56, 223-231; Rossier, J., Reymond, F., Michel, P. E., Electrophoresis 2002, 23, 858-867; Lacher, N. A., Garrison, K. E., Martin, R. S., Lunte, S. M., Electrophoresis 2001, 22, 2526-2536; Vandaveer, W. R. I. V., Pasas, S. A., Martin, R. S., Lunte, S. M., Electrophoresis 2002, 23, 3667-3677; and Wang, J., Trends in Anal. Chem. 2002, 21, 226-232, the entire contents and disclosures of which are hereby incorporated by reference. Since many compounds are electrochemically active, many applications may be found, particularly using direct current (DC) amperometry, see Vandaveer, W. R. I. V., Pasas, S. A., Martin, R. S., Lunte, S. M., Electrophoresis 2002, 23, 3667-3677, the entire contents and disclosure of which is hereby incorporated by reference. However, when a constant potential is applied, the electrode may be fouled by the accumulation of adsorbed carbonaceus material, resulting in an unstable signal, see Fanguy, J. C., Henry, C. S., Analyst 2002, 127, 1021-1023; Garcia, G., Garcia, C. D., Ortiz, P. I., De Pauli, C. P., J. Electroanal. Chem. 2002, 519, 53-59, the entire contents and disclosures of which are hereby incorporated by reference. This effect is particularly detrimental when carbohydrates, thiols or phenols are detected, see Hughes, S., Johnson, D. C., Anal. Chim. Acta 1981, 132, 11-22; and Garcia, C. D., Ortiz, P. I., Electroanalysis 2000, 12, 1074-1076, the entire contents and disclosures of which are hereby incorporated by reference. This problem may be solved with conventional systems by polishing the electrodes to remove build-up or coating the electrodes to prevent build-up, see Kauffmann, J. M., Pekli-Novak, M., Nagy, A., Acta Pharm. Hung. 1996, 66, 57-64; Garcia, C. D., Ortiz, P. I., Electroanalysis 1998, 10, 832-835, the entire contents and disclosures of which are hereby incorporated by reference. To overcome problems associated with electrode fouling in conventional liquid chromatography, a potential waveform referred to as pulsed amperometric detection (PAD) may be applied. In PAD, a high positive potential is applied in order to clean the electrode surface followed by a negative potential step to reactivate the electrode surface. A third, moderate potential is applied for detection of the target analytes. PAD has proven to be effective for a large number of analytes including carbohydrates, amino acids, sulfurs and alcohols, see LaCourse, W. R., Pulsed Electrochemical Detection in High-Performance Liquid Chromatography; Wiley J. & Sons: New York, 1997, the entire contents and disclosure of which is hereby incorporated by reference. PAD is particularly useful when the analyte lacks a strongly-absorbing chromophore (i.e., ultraviolet/visible (UV/Vis) spectrometry) or where other electrochemical techniques are ineffective due to rapid electrode fouling, see Johnson, D. C., Dobberpuhl, D., Roberts, R., Vandeberg, P., J. Chromatogr. 1993, 640, 79-96, the entire contents and disclosure of which is hereby incorporated by reference. Examples where fouling is important include the electrochemical detection of metallic ions, carbohydrates, amines, thiols and alcohols, see Wen, J., Cassidy, R. M., Baranski, A. S., J. Chromatogr., A 1998, 811, 181-192; Lu, W., Cassidy, R., Anal. Chem. 1993, 65, 2878-2881; Deore, B., Yakabe, H., Shiigi, H., Nagaoka, T., Analyst 2002, 127, 935-939; Owens, G. S., LaCourse, W. R., J. Chromatogr., B 1997, 695, 15-25; and LaCourse, W. R., Johnson, D. C., Rey, M. A., Slingsby, R. W., Anal. Chem. 1991, 63, 134-139, the entire contents and disclosures of which are hereby incorporated by reference. These substances are important in a broad range of biological processes and diseases, see Fernandes, J., Saudubray, J. M., Van Den Berghe, G., Inborn Metabolic Diseases: Diagnosis and Treatment, 3rd edition ed., Springer Verlag, 2000, the entire contents and disclosure of which is hereby incorporated by reference. Carbohydrates are not only a significant source of energy for both plants and animals but they also play a substantial role in biological recognition of proteins, see O'Shea, T. J., Lunte, S. M., LaCourse, W. R., Anal. Chem. 1993, 65, 948-951, the entire contents and disclosure of which is hereby incorporated by reference. In addition to being clinically important, amino acids, thiols and alcohols also play an important function assessing the nutritional quality of foods and beverages and give an indication of possible alteration or transformation occurring during food-processing and storage procedures, see Fernandes, J., Saudubray, J. M., Van Den Berghe, G., Inborn Metabolic Diseases: Diagnosis and Treatment, 3rd edition ed., Springer Verlag, 2000; and Casella, I. G., Contursi, M., Desimoni, E., Analyst 2002, 127, 647-652, the entire contents and disclosures of which are hereby incorporated by reference.

SUMMARY

According to a first broad aspect of the present invention, there is provided a microchip that comprises channels formed in a channel forming medium. The main channel is the separation channel. There is also provided a detecting channel, which contains a conductive element for performing electrochemical detection, formed in the channel forming medium and adjoined to the main channel. Finally there are additional channels and reservoirs for injecting sample and buffer during analysis procedures.

According to a second broad aspect of the present invention, there is provided a method for forming a microchip. The microchip is formed by forming a main channel in a channel forming medium; forming a detecting channel in a channel forming medium, wherein the detecting channel adjoins the main channel; forming at least one reservoir in the channel forming medium, wherein the reservoir adjoins at least one of the main channel and the detecting channel; placing a first conductive element in the detecting channel; and placing a second conductive element in the reservoir to thereby form the microchip.

According to a third broad aspect of the invention, there is provided a method for performing electrophoresis. Electrophoresis is performed by attaching at least a first conductive element and a second conductive element to a microchip having a biologic microfluid thereon, wherein the microchip comprises at least one main channel formed in a channel forming medium, the main channel containing at least one biologic microfluid; at least one detecting channel containing the first conductive element for performing electrochemical detection, the detecting channel being formed in the channel forming medium and adjoining the main channel; and at least one reservoir containing the second conductive element for serving as a reference to the first conductive element, the reservoir being formed in the channel forming medium and containing biologic waste; and applying either continuous or pulsed amperometric detection to the microchip using the conductive elements to thereby cause biologic specimens within the biologic microfluid to migrate toward the first conductive element and, when in electrical contact with the first conductive element, to generate a measurable signal.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 3 is a table for pulsed amperometric detection parameters for the detection of carbohydrates, amino acids and antibiotics, cleaning: 0.05 s, reactivation: 0.025 s, and detection 0.15 s;

FIG. 4 is a table of potentials applied and solution in each reservoir on a microchip during either an injection or a separation step;

DETAILED DESCRIPTION

Figure 1:
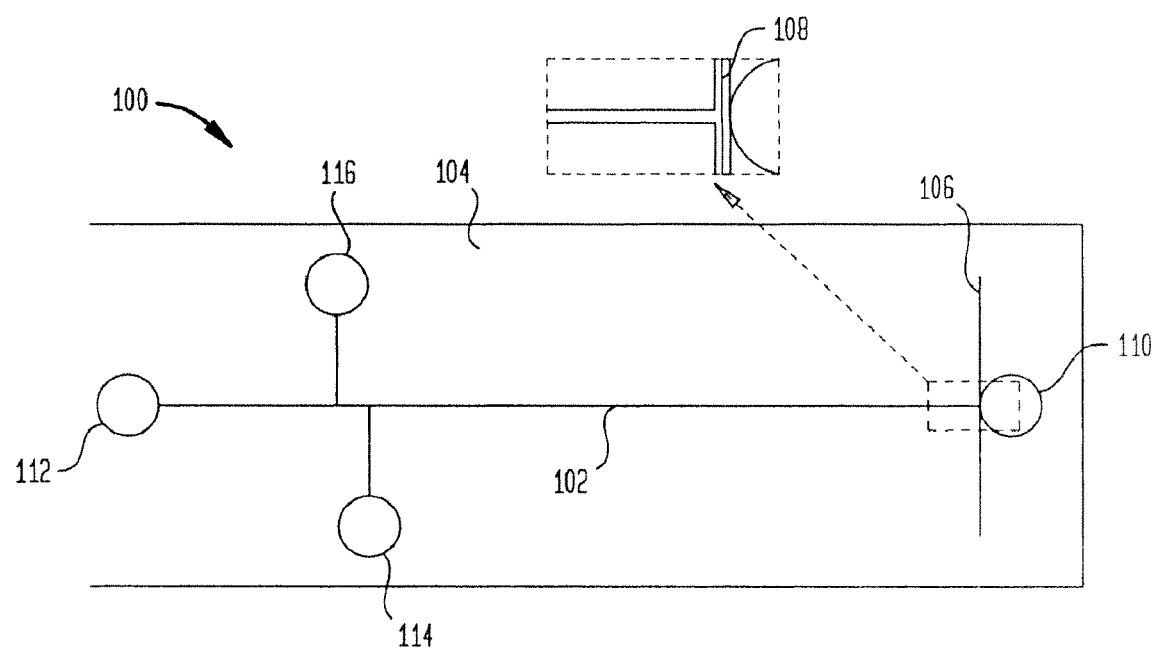
FIG. 1 is a schematic diagram of a capillary electrophoresis chip with pulsed amperometric detection, which is constructed in accordance with an embodiment of the present invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "microchip" refers to one or more closed or environmentally isolated or controlled devices capable of performing electrophoresis under various dimensions.

For the purposes of the present invention, the term "channel forming medium" refers to one or more material from which channels are formed for a microchip. The channels may be formed by impression, molding, etching, etc.

For the purposes of the present invention, the term "main channel" refers to one or more primary channels where microfluids are stored, separated and/or analyzed. The majority of the detected elements within the device originate from the main channel.

For the purposes of the present invention, the term "biologic microfluids" refers to one or more specimens introduced into a microchip for analysis via electrophoresis. Biologic microfluids may include carbohydrates, amino acids, antibiotics, proteins, etc.

For the purposes of the present invention, the term "detecting channel" refers to one or more secondary channels that adjoin a main channel. A detecting channel contains the primary conductive element for performing electrophoresis. A detecting channel also contains biologic microfluids due to its adjoining to the main channel. A detecting channel may intersect the main channel at an endpoint of the main channel or between the end points of the main channel. Further, a detecting channel may intersect or contact the main channel at an angle ranging from 0 to 180 degrees.

For the purposes of the present invention, the term "conductive element" refers to a material used to perform continuous or pulsed amperometric detection by inducing a component of a biologic fluid to move under the influence of an applied electric field across conductive elements.

For the purposes of the present invention, the term "reservoir" refers to an opening connected to a microfluidic channel in which a solution may be added.

For the purposes of the present invention, the term "biologic waste" refers to a solution that has been analyzed.

For the purposes of the present invention, the term "mold" refers to one or more patterns used to form channels and reservoirs. A mold of the present invention may be in the form of a mold, a mask, etc.

For the purposes of the present invention, the term "sealing medium" refers to one or more secondary materials used to enclose channels and reservoirs formed in a channel forming medium. A sealing medium of the present invention may be the same material as the channel forming medium or different. A sealing medium is equivalent to a channel forming medium if the microchip made from the sealing medium is of unibody construction.

Description

The present invention provides a configuration for a microchip that performs electrophoresis. An ideal electrochemical detector should ensure well-defined mass transport, minimal band broadening and electrical isolation from the high separation voltage. Additional requirements are high sensitivity, simple handling, and long term stability, see Verpoorte, E., Electrophoresis, 2002, 23, 677-712; Wang, J., Talanta 2002, 56, 223-231; Rossier, J., Reymond, F., Michel, P. E., Electrophoresis, 2002, 23, 858-867; Lacher, N. A., Garrison, K. E., Martin, R. S., Lunte, S. M., Electrophoresis, 2001, 22, 2526-2536; Vandaveer, W. R. I. V., Pasas, S. A., Martin, R. S., Lunte, S. M., Electrophoresis, 2002, 23, 3667-3677; and Wang, J., Trends in Anal. Chem., 2002, 21, 226-232, the entire contents and disclosures of which are hereby incorporated by reference. Various detector configurations based on different capillary/working electrode arrangements have been reported to perform electrochemical detection on microfluidic devices, see Wang, J., Talanta, 2002, 56, 223-231, the entire contents and disclosure of which is hereby incorporated by reference.

A schematic of a microchip 100 of the present invention is shown in FIG. 1. FIG. 1 shows a basic embodiment of the present invention in which a main channel 102 has been formed in a channel forming medium 104. Channel forming mediums of the present invention may comprise poly(dimethylsiloxane) (PDMS) and/or poly(methylmethacrylate) (PMMA). In operation, main channel 102 contains buffer for separation. Reservoirs 110, 112, and 116 contain buffer while reservoir 114 contains sample. To initiate analysis, sample is moved from reservoir 114 to reservoir 116 through the connecting channel by either voltage or pressure. For separation, voltage is applied between reservoir 112 and reservoir 110 to mobilize the buffer and separate the analytes. Microchip 100 also comprises a detecting channel 106 containing a conductive element 108 (in inset) for performing electrochemical detection. Although detecting channel 106 is shown in an end-column configuration, one or more detecting channels of the present invention may be at various locations along or in the main channel. Suitable conductive elements of the present invention include gold, platinum, palladium, copper, nickel, and nickel-alloy wires and carbon fibers or paste. Reservoir 110 contains a second conductive element (not shown) that serves as a reference electrode. Reservoir 110 collects waste from the use of microchip 100. One or more additional ground electrodes may be added to the system as well.

A chip of the present invention, in embodiments, has dimensions of approximately 25×75 mm, although the dimensions may vary depending on the particular application or embodiment, including channels that may vary in length from about 0.5 to about 8 cm long, about 10 to about 150 microns wide and about 5 to about 100 microns deep.

According to an embodiment of the present invention, a double-T injector, as defined by the two side channels, with a 580 μm gap between side channels (1.3 nL) was used in an application of the present invention. However, the device of the present invention is compatible with any type of known microchip injector and may be accordingly modified in light of the teachings of the present application. In such an embodiment, exemplary channels may be approximately 50 μm wide, approximately 50 μm deep, and approximately 4-5, for example 4.5, cm long.

Figure 2:
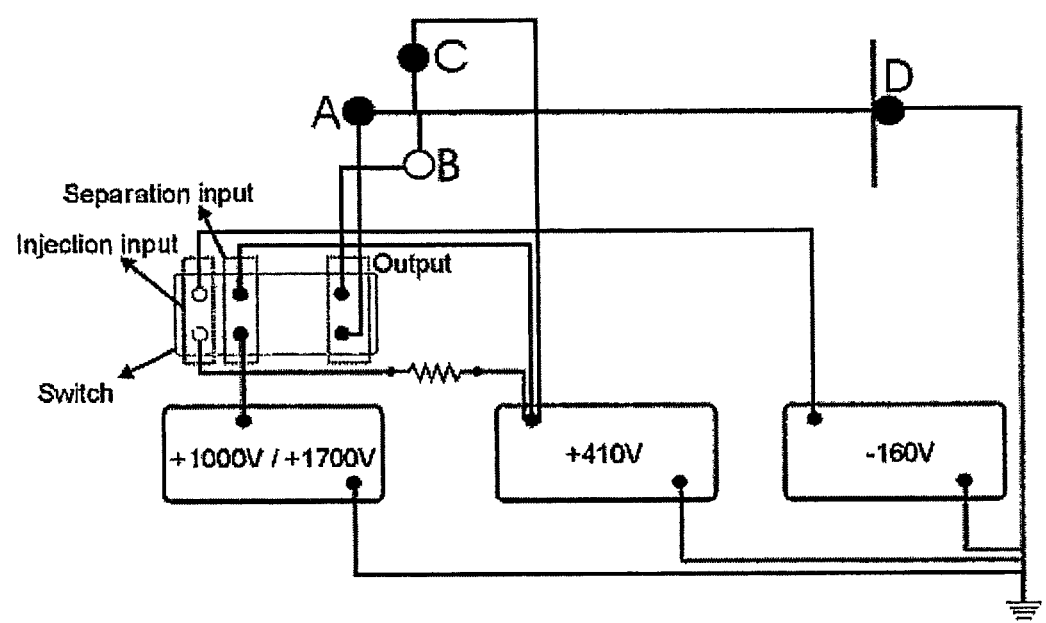
FIG. 2 is a schematic diagram of electric circuitry for performing electrokinetic injection/separation in accordance with FIG. 1.

The present invention also provides circuitry to control a microchip of the present invention. Three power supplies were connected using a three position switch according to FIG. 2. A 1MΩ resistor was also included to avoid joule heating during the injection procedure. A 1MΩ resistor was used as an exemplary resistor, but the resistance may vary depending on the particular embodiment or application in accordance with the teachings of the present application. Electrical connections were made to the microfluidic devices with platinum electrodes placed into reservoirs at the ends of each channel. FIG. 2 shows an operational schematic for injection and separation using a power supply. Voltages are provided to inject (left hand numbers) and separate (right hand numbers).

The microchip of the present invention satisfies most of the needs for this type of device and also allows the isolation of the detector from the separation current through the detector-column configuration. In addition, the position of the working electrode may be precisely and reproducibly arranged without the need for an XYZ positioner, similar to a microfabricated electrode. An increase in electrode area in contact with solution (with respect to planar electrodes) may also be achieved by utilizing a cylindrically shaped electrode without necessarily an increase in electrode width.

The microchip of the present invention is similar to two other microchip capillary electrophoresis (CE) systems reported previously, see Martin, R. S.; Gawron, A. J., Lunte, S. M.; Henry, C. S. Analytical Chemistry, 2000, 72, 3196-3202; Schwarz, M. A.; Galliker, B.; Fluri, K.; Kappes, T.; Hauser, P. C. Analyst 2001, 126, 147-151, the entire contents and disclosures of which are hereby incorporated by reference. Martin, et al., reported the use of carbon fibers used as working electrodes for end-channel and in-channel detection of catechol, sodium nitrite and cyanobenz[f]-isoindole-glycine. In that design, electrodes were immobilized in a separate PDMS layer and only accessed solution on the bottom of the separation channel. The present invention distinguishes itself from Martin, et al., by placing the electrode within an intersecting detecting channel, which increases electrode area that is exposed to the solution. Further the present invention enables the detection of amines, thiols, alcohols and carbohydrates. The second similar design was reported by Schwarz, et al. In that report, microwires were aligned in an etched cavity, at the end of the separation channel. The present invention distinguishes itself from Schwarz, et al., by placing the detecting electrode in an intersecting channel that is formed, for example, via a molding process. Thus, the present invention removes the need for an XYZ positioner to achieve electrode alignment and may be adapted to dual electrode detection.

The present invention also provides a method to produce a microchip that performs electrophoresis. A method of forming a microchip comprises forming a main channel in a channel forming medium; forming a detecting channel in a channel forming medium, wherein the detecting channel adjoins the main channel; forming at least one reservoir in the channel forming medium, wherein the reservoir adjoins at least one of the main channel and the detecting channel; placing a first conductive element in the detecting channel; and placing a second conductive element in the reservoir to thereby form the microchip.

According to an embodiment of the present invention, a 76 mm silicon wafer (Silicon Valley Microelectronics Inc.) was cleaned and oxidized with piranha solution ($2:1 H_2SO_4:H_2O_2$). The wafer was then coated with SU-8 2035 negative photoresist using a spin coater by dispensing approximately 3 mL of photoresist. A spread cycle of 500 rpm for 10 seconds followed by 2500 rpm for 30 seconds was performed followed by two pre-exposure baking steps at 65° C. and 95° C. for 5 and 10 minutes, respectively. A digitally produced mask containing the channel pattern was placed on the coated wafer, exposed to light via a near-UV flood source for 150 seconds and then baked at 95° C. for 13 minutes. The positive relief was developed by placing the wafer in propylene glycol methyl ether acetate for 15 minutes, rinsing with methanol, and drying under a $N_2$ stream. The height of the positive patterns on the molding masters, which are equal to the channel depths created on the PDMS layer, was 50 μm when measured with a profilometer. Two PDMS layers were fabricated by pouring a degassed mixture of Sylgard 184 silicone elastomer and curing agent (10:1) onto either a molding master or a blank wafer, followed by curing for at least 2 hours at 65° C. The cured PDMS was separated from the mold and reservoirs were made at the end of each channel using a 6 mm circular punch. After that, a 25 μm gold wire was aligned at the end of the separation channel in a perpendicular channel designed for that purpose (see, for example, FIG. 1). Next, the two PDMS layers were placed in an air plasma cleaner (Harrick plasma cleaner/sterilizer PDC-32G), oxidized for 20 seconds and immediately brought into conformal contact to form an irreversible seal. This seal was sufficiently strong that the two pieces could not be separated without destroying the assembled microchip. Finally, the extremities of the electrode channel were sealed with two drops of glue and an electrical connection was made using silver paint and a copper wire.

The present invention also provides a method of performing electrophoresis using a microchip of the present invention. A method of performing electrophoresis comprises attaching at least a first conductive element and a second conductive element to a microchip having a biologic microfluid thereon, wherein the microchip comprises at least one main channel formed in a channel forming medium, the main channel containing at least one biologic microfluid; at least one detecting channel containing the first conductive element for performing electrochemical detection, the detecting channel being formed in the channel forming medium and adjoining the main channel; and at least one reservoir containing the second conductive element for serving as a reference to the first conductive element, the reservoir being formed in the channel forming medium and containing biologic waste; and applying either continuous or pulsed amperometric detection to the microchip using the conductive elements to thereby cause biologic specimens within the biologic microfluid to migrate toward the first conductive element and, when in electrical contact with the first conductive element, to generate a measurable signal.

Electrochemical detection may be performed by Mode I (or pulsed amperometric detection at an oxide free surface) using a two-electrode setup. A gold, platinum or other suitable material may be used as a working electrode and the corresponding detection potential may be optimized for each compound. The second electrode, used as a reference and auxiliary, may be, for example, a platinum wire placed in the waste reservoir (see FIGS. 1 and 2). A separate ground electrode may be used for the separation system. A similar two-electrode approach was previously presented by Schwarz et al. in which the authors successfully demonstrated the possibility to perform detection with the working and the separation ground electrode only using a custom-made potentiostat, see Schwarz, M. A., Galliker, B., Fluri, K., Kappes, T., Hauser, P. C., Analyst, 2001, 126, 147-151, the entire contents and disclosure of which is hereby incorporated by reference. However, an intense baseline ($\mu$A) noise is obtained if a standard electrochemical detector is used. The potentials applied to clean the electrode and reconstruct the surface were optimized in order to minimize the post-peak dip, see LaCourse, W. R. Pulsed Electrochemical Detection in High-Performance Liquid Chromatography; Wiley J. & Sons: New York, 1997, the entire contents and disclosure of which is hereby incorporated by reference. PAD was performed according to the potential scheme described below and shown in FIG. 3. The typical potentials used during injection and separation are summarized in FIG. 4. These voltages may range from about 100 V to about 5000V depending on the specific chip in use.

EXAMPLES

Example I

Injection Procedure

A solution of 1 $\mu$M fluorescein, prepared in the running electrolyte, was used to follow the injection. For the present experiments, injection times of 10 seconds were used to ensure plug homogeneity because at the slowest electroosmotic flow (EOF) conditions, the double-T was filled in 7 seconds. Injection times are dependent on the sample and the chip and may vary from about 1 second to about 1 minute.

Example II

Analysis of Carbohydrates

Figure 5:
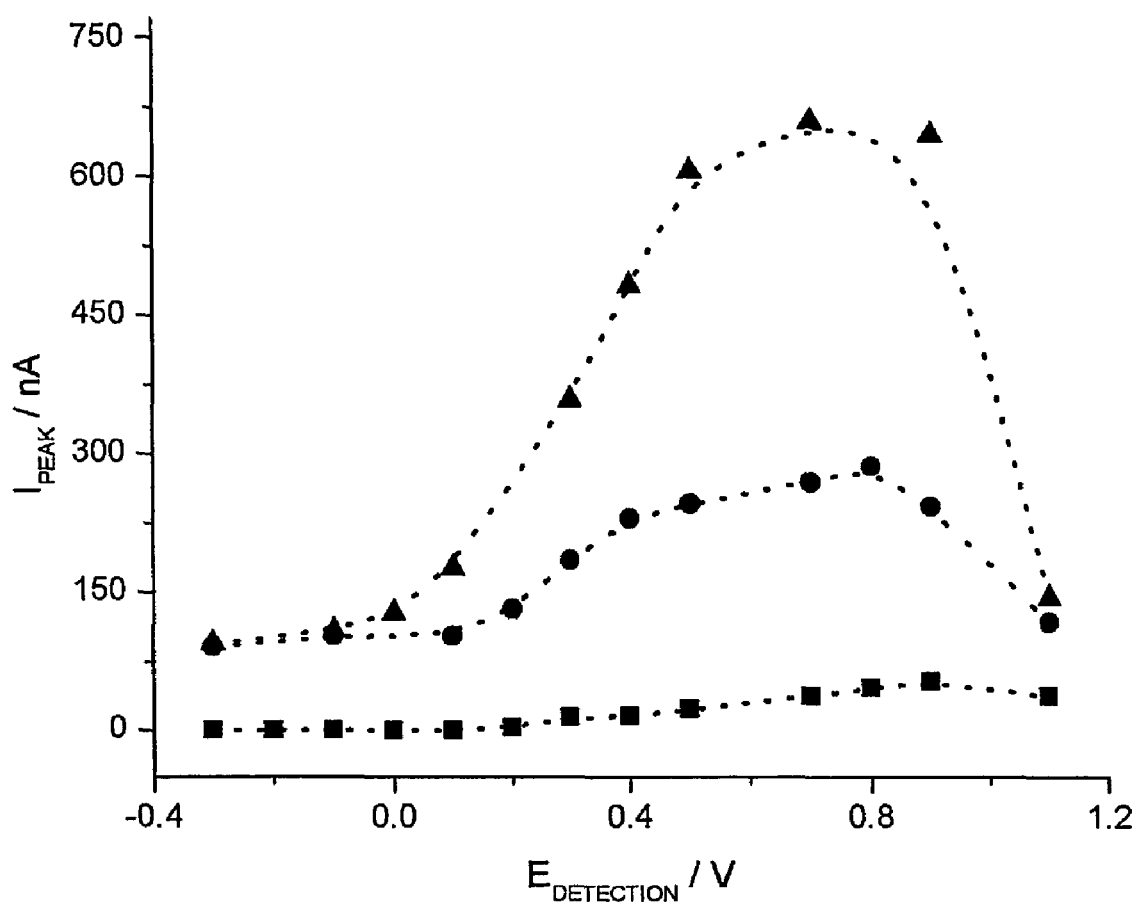
FIG. 5 illustrates the effect of detection potential on a signal for analyzing carbohydrates, with (--▲--) representing GLU, (--●--) representing LAC and (--■--) representing sucrose, with the following conditions: 10 mM borate buffer pH=12.00, separation potential=+1700V (A-D), and a 10 second injection timeframe.

It is well known that activation barriers for oxidation of some compounds may be decreased at a clean Au electrode, see LaCourse, W. R., Pulsed Electrochemical Detection in High-Performance Liquid Chromatography, Wiley J. & Sons: New York, 1997, the entire contents and disclosure of which is hereby incorporated by reference. These surfaces stabilize free-radical oxidation products by adsorption and, thereby, may promote faradaic reactions. Once a clean surface is obtained, a potential should be chosen in order to maximize the electrode response. The effect of the detection potential on the signal was analyzed between −0.3 to +1.1V for glucose (GLU), lactose (LAC) and sucrose (SUC) as shown in FIG. 5. As may be seen, the peak current increases as the potential increases until a maximum in the signal is obtained. The following current decrease observed at higher potentials may be explained as the result of the formation of oxide on the working electrode surface during the measurement step. When the applied potential allows the formation of the superficial oxides, the oxidation of the analytes may be inhibited. Since similar profiles were found for all carbohydrates, +0.7V may serve as a suitable detection potential.

The majority of the separations of carbohydrates by CE are based on their degree of dissociation at alkaline conditions (pH>12), see Hu, Q., Zhou, T., Hu, G., Fang, Y., J. Pharm. Biomed. Anal., 2002, 30, 1047-1053, the entire contents and disclosure of which is hereby incorporated by reference. Alkaline pH ($\geq$12) is also useful for PAD of carbohydrates. Unfortunately, changes in the pH of the electrolyte (NaOH) in the range from 11.80 to 12.70 were not enough to accomplish complete separation of the carbohydrates on PDMS microchips (data not shown). A pH of 12.00 was chosen for the analysis of the other variables because some separation was seen under these conditions.

Organic solvents have been widely used to improve separations by either liquid chromatography (LC) or CE, see Soga, T., Inoue, Y., J. Chromatogr., 1993, 620, 175-181; and Takizawa, K., Nakamura, H., Anal. Sci., 1998, 14, 925-928, the entire contents and disclosures of which are hereby incorporated by reference. In the case of CE, the resolution enhancement results from a change in the viscosity of the electrolyte and the resulting change in the electroosmotic flow (EOF). However, the addition of 5% v/v of different alcohols (methanol, ethanol, 1-propanol, 1-butanol) or 7.5% v/v acetonitrile to the running solution (NaOH, pH=12.00) did not show a significant impact on the separation efficiency. Furthermore, the addition of organic solvents resulted in a decrease in the signal magnitude and an increase in the baseline noise (data not shown). This may be explained by the fact that aliphatic alcohols may be detected by PAD. In the case of the acetonitrile, it may be adsorbed to the electrode surface decreasing the number of active sites for analyte adsorption, see LaCourse, W. R., Pulsed Electrochemical Detection in High-Performance Liquid Chromatography, Wiley J. & Sons: New York, 1997, the entire contents and disclosure of which is hereby incorporated by reference. For these reasons, the modification of the buffer with organic solvents was not further pursued.

Figure 6:
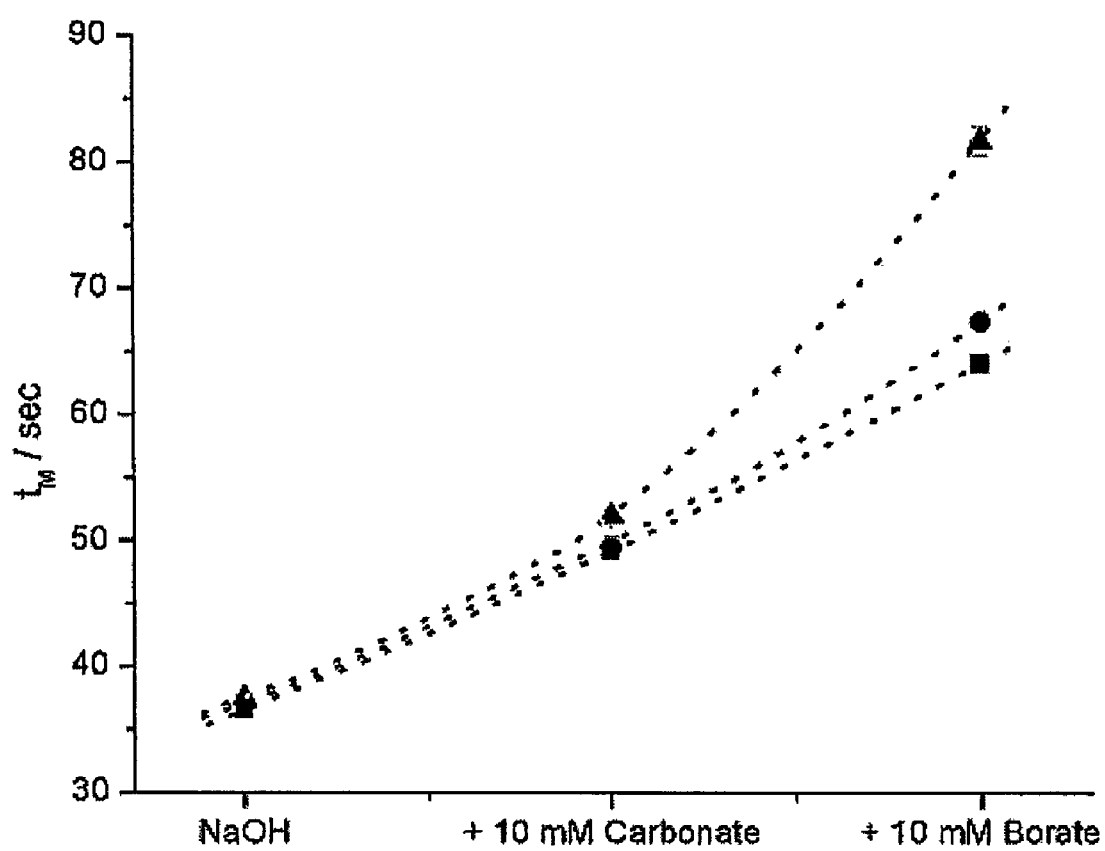
FIG. 6 illustrates the effect of typical electrolyte solutions on migration times for analyzing carbohydrates, with (--▲--) representing 0.8 mM GLU, (--●---) representing 1.6 mM LAC and (--■--) representing 2.0 mM MAN, with the following conditions: pH=12.00, separation potential=+1700V (A-D), and a 10 second injection timeframe.

It was previously reported that the complexation of borate with hydroxyl groups may improve the resolution of carbohydrates, see Stefansson, M., Westerlund, D., J. Chromatogr., 1993, 632, 195-200, the entire contents and disclosure of which is hereby incorporated by reference. In order to study the effect of a secondary electrolyte on resolution, electrolyte solutions containing 10 mM borate (pH=12.00) were prepared. Experiments using 10 mM carbonate (pH=12.00) as a running electrolyte (as reported previously) were performed for comparison purposes, see Fanguy, J. C., Henry, C. S., Analyst 2002, 127, 1021-1023, the entire contents and disclosure of which is hereby incorporated by reference. The migration times as a function of the electrolyte is shown in FIG. 6. As may be observed, electropherograms obtained in 0.01M NaOH resulted in the shortest migration times but a severe overlap of the peaks occurred. When 10 mM $K_2CO_3$ was added to the electrolyte, longer migration times and a slight improvement of the resolution were achieved. The improvement was most likely due to a reduction in the EOF as a result of an increase in the ionic strength of the solution. The best separation was achieved when 10 mM borate pH=12.00 was used as a running electrolyte. The improvement in resolution is likely the result of two factors, complexation of the carbohydrates with the borate present in the running solution and a further increase in the ionic strength that results from the use of borate as opposed to boric acid.

Figure 7:
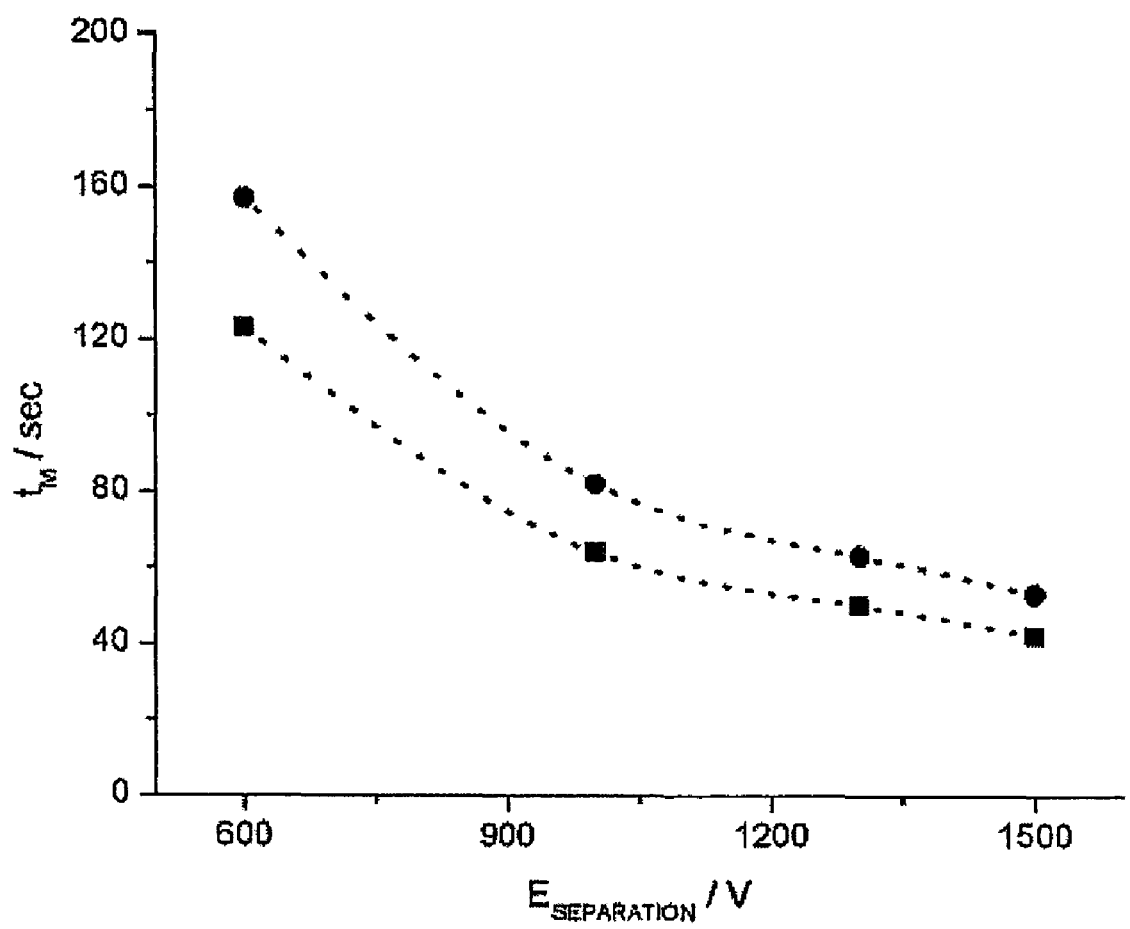
FIG. 7 illustrates the effect of separation potential on migration times for analyzing carbohydrates, with (--■--) representing 0.8 mM GLU, and (--●--) representing 2.0 mM MAN, with the following conditions: 10 mM borate buffer pH=12.00, detection potential=0.7V, and a 10 second injection timeframe.

Applied potential may be used to control EOF and separation resolution in CE. Applied potential may not only partially control the separation process but also the amount of time that the analytes spend in the detection zone. In order to evaluate the effect of potential, migration times of a mixture of glucose and mannose were measured as a function of the separation potential between +600 and +1500 V (FIG. 7). As may be observed, a clear separation of both compounds may be obtained in the whole range of studied potentials and, at +1500 V both compounds may be separated in less than 60 seconds. If lower separation potentials are applied, longer runs and less noisy baselines are achieved. In addition, higher peak currents were obtained due to the increase in the residence time at the electrode. As a compromise between the analysis time and the signal/noise ratio, +1000 V was chosen as a separation potential for the separation of carbohydrates under the present conditions.

Figure 8:
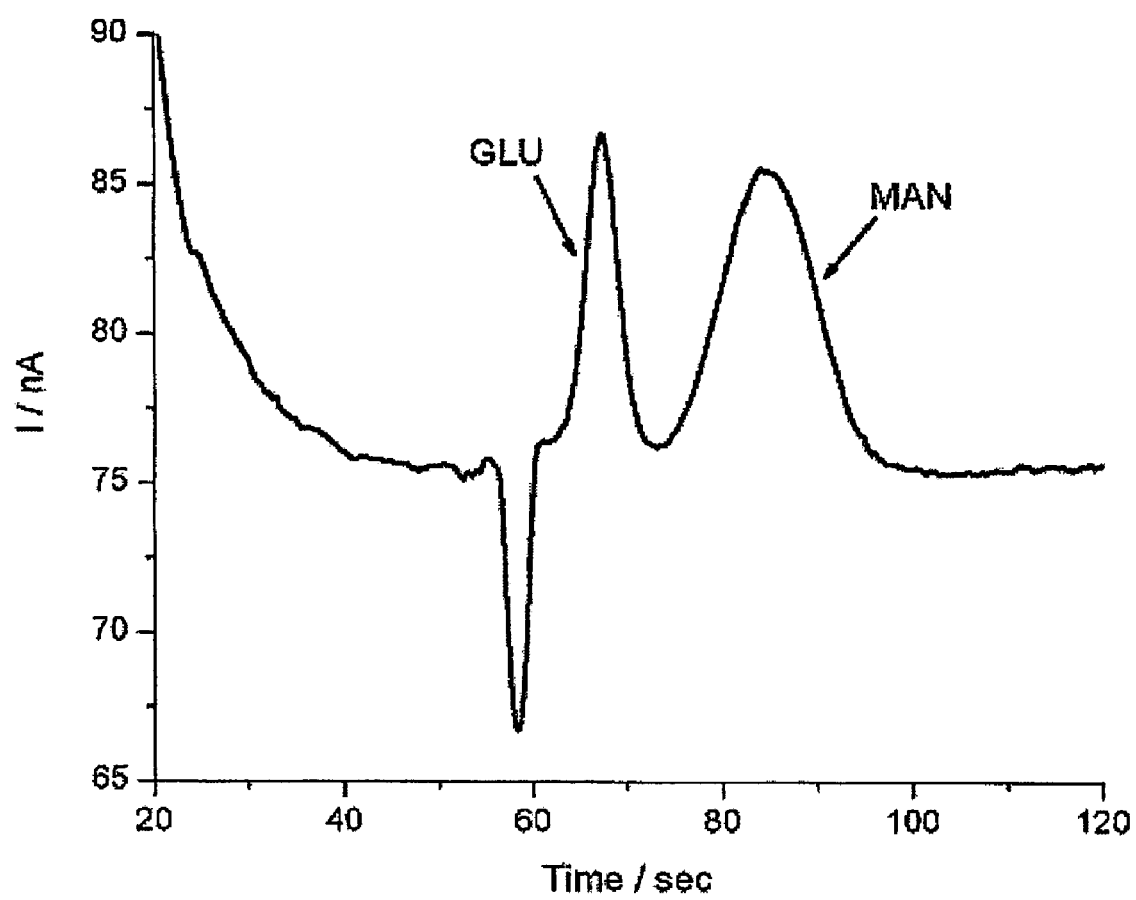
FIG. 8 illustrates an electropherogram obtained by an embodiment of the present invention for analyzing carbohydrates, with the following conditions: 0.8 mM GLU, 2.0 mM MAN, 10 mM borate buffer pH=12.00, separation potential=+1700V, detection potential=0.7V, and a 10 second injection timeframe.

In FIG. 8, an electropherogram for a mixture of 0.8 mM glucose (GLU) and 2.0 mM mannose (MAN) using 10 mM borate (pH=12.00), +1000 V as the separation potential and +0.7 V as the detection potential is shown. As may be observed, the combination of the decrease in EOF and the interaction between the borate and the carbohydrates allows baseline resolution of the carbohydrates showing also the improvement with respect to previously presented results, see Fanguy, J. C., Henry, C. S., Analyst, 2002, 127, 1021-1023, the entire contents and disclosure of which is hereby incorporated by reference. The migration times for GLU and MAN were 67.0±1.3 seconds and 84.5±1.5 seconds respectively (n=3). In FIG. 8, a dip is observed before the first oxidation peak. Since this negative peak was observed only when new chips were used, it may be attributed to a leakage of unpolymerized PDMS monomer or cross-linker.

Example III

Analysis of Amino Acids

The direct detection of unlabeled amino acids has the potential to simplify quantification of these important analytes. The effect of the potential applied to the working electrode was analyzed between −0.3 and +1.1V for the three amino acids (data not shown). As was observed for carbohydrates, the peak current increased as the potential increased until a maximum in the signal was obtained at around 0.7V. Since similar profiles were found between the selected amino acids, 0.7V was chosen as a suitable detection potential. As part of the detection potential determination, a higher cleaning potential was selected when sulfur-containing compounds were injected in order to decrease the peak tailing produced by the high interaction between the sulfur group and the Au.

The electrolyte conditions may not only affect the separation process but also the detection step. It was previously reported that the adsorption of the amines through the free pair of electrons may be required prior to their electrocatalyzed oxidations, see LaCourse, W. R., Pulsed Electrochemical Detection in High-Performance Liquid Chromatography, Wiley J. & Sons: New York, 1997, the entire contents and disclosure of which is hereby incorporated by reference. It has also been found that amine oxidation is surface-oxide catalyzed; therefore at the higher pH values, higher current peaks may be obtained, see LaCourse, W. R., Pulsed Electrochemical Detection in High-Performance Liquid Chromatography, Wiley J. & Sons: New York, 1997, the entire contents and disclosure of which is hereby incorporated by reference. However, in order to maximize the differences in ionization between the three selected compounds, a lower pH value 10 mM borate (pH=9.45) was chosen as the working buffer. This solution also decreased the EOF, allowing a better separation of the compounds.

Figure 9:
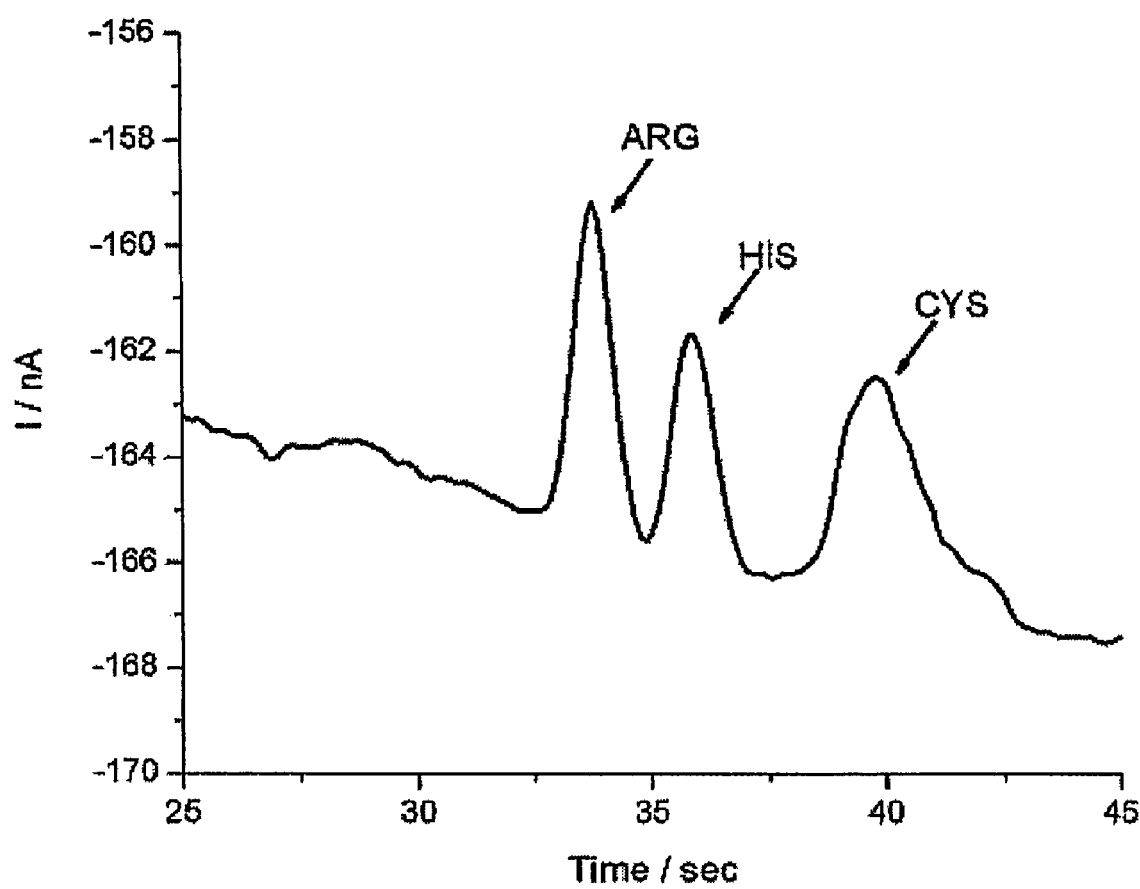
FIG. 9 illustrates an electropherogram obtained by an embodiment of the present invention for analyzing amino acids, with the following conditions: 0.24 mM Arg, 0.70 mM His, 0.03 mM Cys, 10 mM borate buffer pH=9.45, separation potential=+1700V, detection potential=0.7V, and a 10 second injection timeframe.

Because a lower conductivity electrolyte was used in order to separate the amino acids (10 mM borate, pH=9.45), higher electric fields may be used to drive the separation process. The effect of the separation potential on the migration time was studied between +600 and +2500V for arginine (Arg), histidine (His) and cysteine (Cys) (not shown). A separation potential of +1700V was chosen since clear separations may be achieved in less than 45 seconds for the mixture of Arg/His/Cys under these conditions. A typical electropherogram showing baseline separation of three unlabeled amino acids at the optimized conditions is shown in FIG. 9. The reproducibility of the peak heights were 95%, 95% and 94% for Arg, His and Cys respectively (n=3).

Example IV

Analysis of Antibiotics

Figure 10:
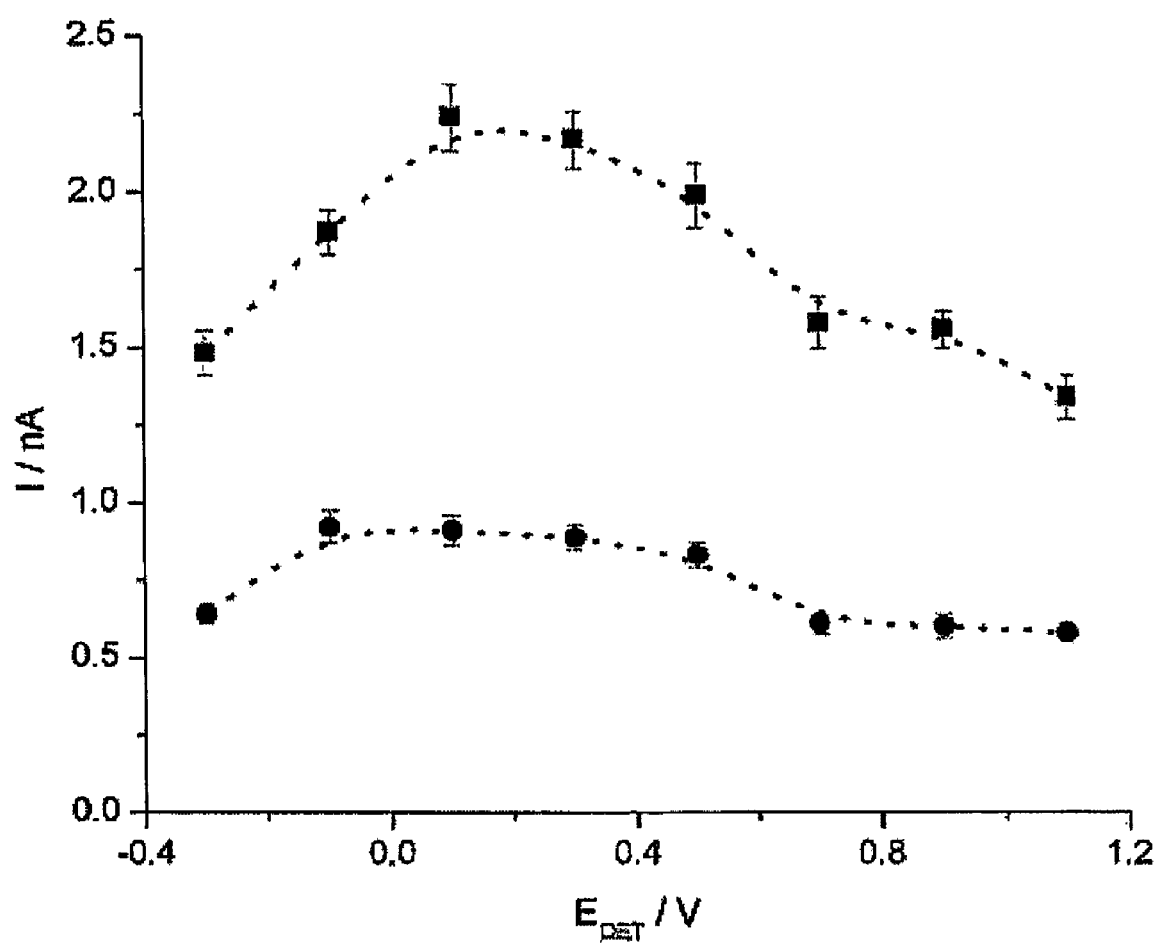
FIG. 10 illustrates the effect of detection potential on a signal for analyzing antibiotics, with (--■--) representing 12 µM PEN and (--●--) representing 13 µM AMP, with the following conditions: 10 mM borate buffer pH=9.45, separation potential=+1000V (A-D), and a 10 second injection timeframe.

The effect of the potential applied to the working electrode was analyzed between −0.3 and +1.1V for the two sulfur-containing antibiotics. In FIG. 10, the hydrodynamic voltammograms for two antibiotics are shown. As was observed for carbohydrates, the peak current increases as the potential increases until a maximum in the signal is obtained, followed by a current decrease at higher potentials (>0.5V). According to this behavior, 0.5V was selected in order to obtain a clear catalytic signal of both penicillin G potassium salt (PEN) and ampicillin (AMP) while also allowing for the detection of other compounds (amino acids or carbohydrates) during the same run.

Figure 11:
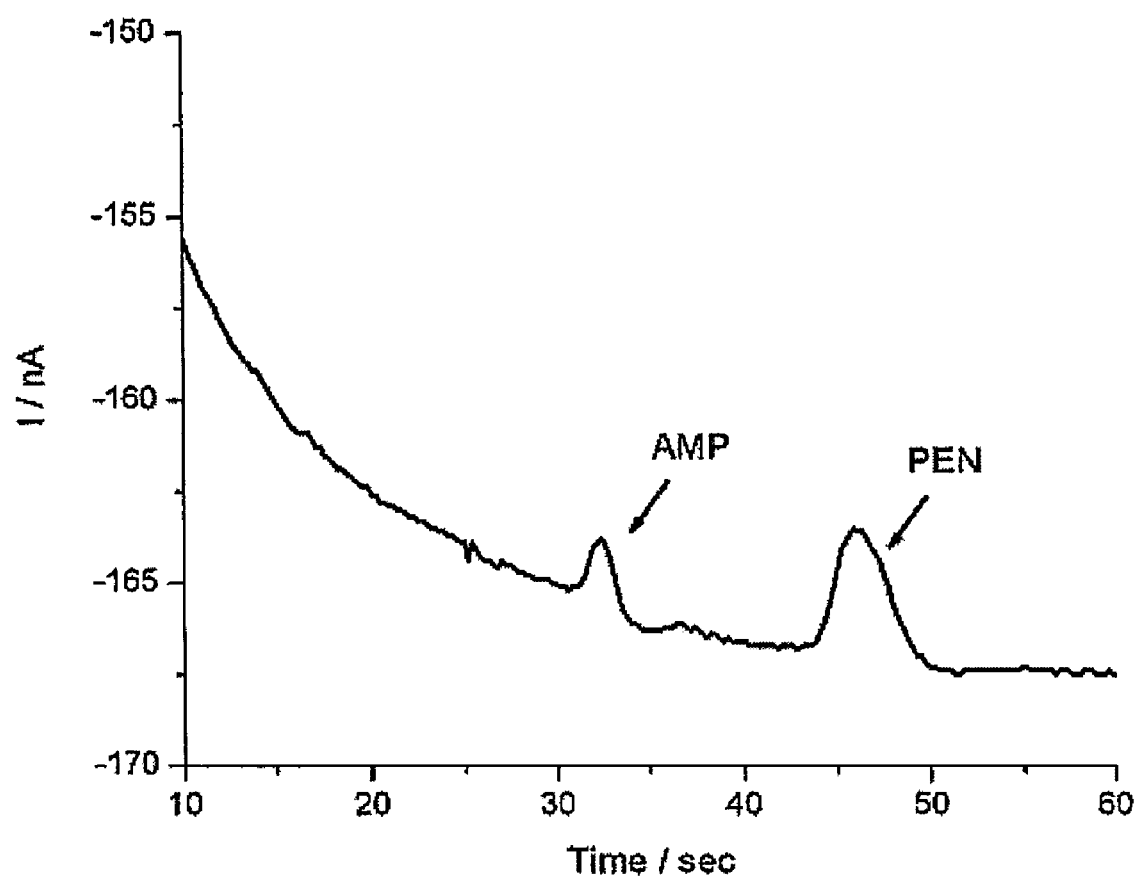
FIG. 11 illustrates an electropherogram obtained by an embodiment of the present invention for analyzing antibiotics, with the following conditions: 13 μM AMP, 12 μM PEN, 10 mM borate buffer pH=9.45, separation potential=+1700V, detection potential=0.5V, and a 10 second injection timeframe.

It is well known that sulfur-containing compounds are electroactive in either acid or alkaline solutions. In order to enhance the separation, the same conditions used for the separation of amino acids were used for the separation of AMP and PEN. The corresponding electropherogram for the separation of the unlabeled antibiotics is shown in FIG. 11 to demonstrate the separation and direct detection of these compounds. As may be observed, a clear separation of the mixture of AMP and PEN was completed in less than one minute. The corresponding migration times for AMP and PEN were 32.3±0.1 seconds and 46.1±0.1 seconds respectively (n=3). It should also be noted in FIG. 11 that the background current decreases with time as the result of electrode equilibration that occurs after injection.

Example V

Limits of Detection

Taking glucose as a model carbohydrate, the response of the detector as a function of the concentration was studied in the 90-1800 µM range. A linear relationship between the concentration and the peak current was obtained in the studied concentration range using the previously optimized conditions. The slope of the calibration curve was 43 nA/mM (R=0.98), with 90 µM as the measured detectable limit. The limit of detection was also studied for mannose and was found to be 150 µM (signal/noise ratio>3).

Unlabeled Arg and His were detectable at concentrations above 100 µM and 350 µM respectively. However, a limit of detection of 10 µM was achieved for Cys because sulfur-containing compounds may exchange more electrons/mol than only amine-containing substances, see LaCourse, W. R., Pulsed Electrochemical Detection in High-Performance Liquid Chromatography, Wiley J. & Sons: New York, 1997, the entire contents and disclosure of which is hereby incorporated by reference. As mentioned before, in order to maximize separation, the analysis of amino acids was performed at a pH value that does not favor the formation of the superficial oxide resulting in the higher limits of detection of the non-sulfur-containing amino acids. Both AMP and PEN were detectable at 5 µM, with a signal/noise ratio equal to 3. Using the optimized conditions and taking into account the injected sample volume (1.3 nL), the mass limits of detection are in the range of 455 fmols for His to 6 fmols for both antibiotics.

Example VI

Figure 12:
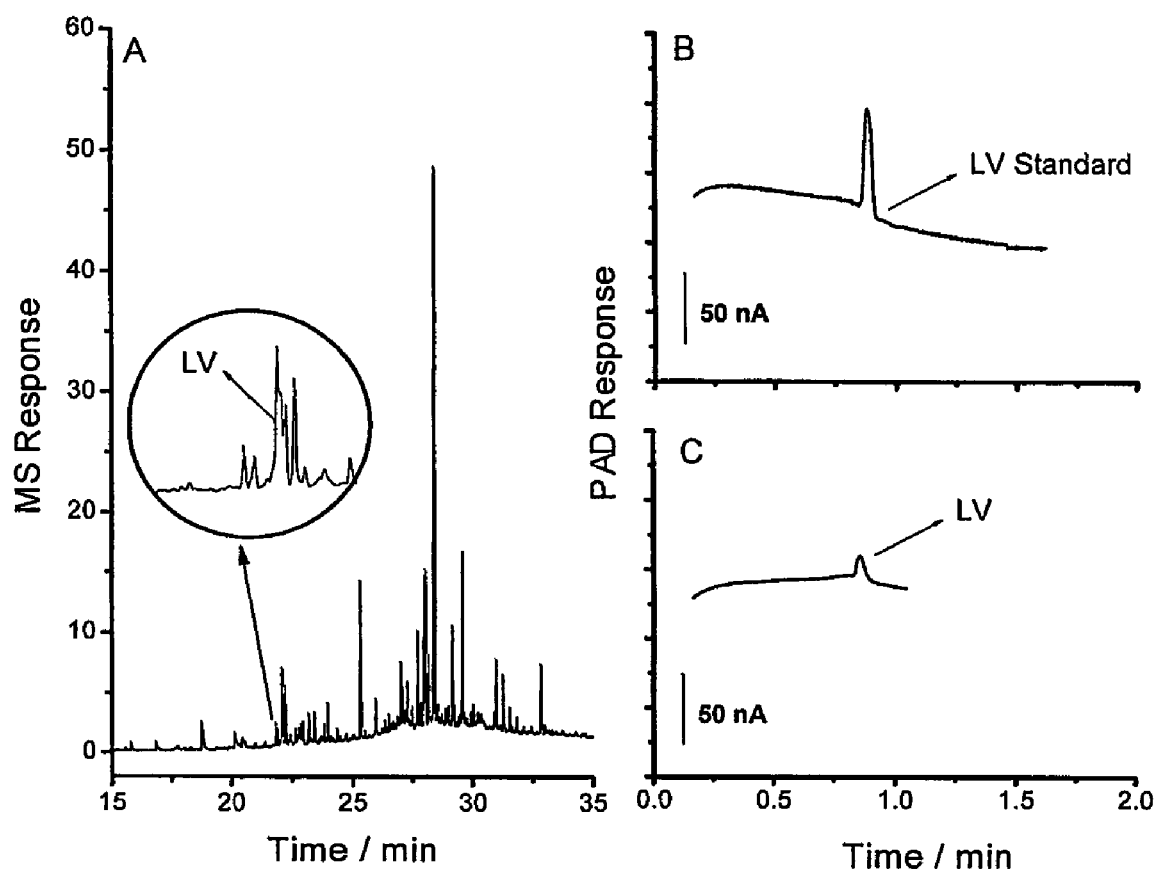
FIG. 12 shows a comparison of the analysis of smoke particulate extracts by two methodologies; A) GC/MS analysis, with the insert showing the peak corresponding to levoglucosan at 22.1 minutes, B) Microchip-CE-PAD analysis of a levoglucosan standard, and C) Microchip-CE-PAD analysis of the smoke extract.

Determination of Levoglucosan from Smoke Samples Using Microchip Capillary Electrophoresis with Pulsed Amperometric Detection The separation and detection of native anhydrous carbohydrates derived from the combustion of biomass using an electrophoretic microchip with pulsed amperometric detection (PAD) is described in the present example. Levoglucosan represents the largest single component of the water extractable organics in smoke particles and may be used to trace forest fires or discriminate urban air pollution sources. Detection of levoglucosan and other sugar anhydrides in atmospheric aerosol samples is typically performed by gas chromatographic (GC) separation with mass spectrometric (MS) detection. This method is cost, time and labor intensive, typically involving a multi-step solvent extraction, chemical derivatization and finally, analysis by GC/MS. However, it provides a rich wealth of chemical information as the result of the combination of a separation method and MS. In contrast, microchip capillary electrophoresis according to the present invention offers the possibility of performing simpler, less expensive and faster analysis. In addition, integrated devices may be fabricated and incorporated with portable computers to perform on-site analysis. In the present example, the effect of the separation potential, buffer pH and composition, injection time and pulsed amperometric detection parameters were studied in an effort to optimize both the separation and detection of anhydrous sugars. Matrix effects were also studied to allow direct measurements from tropospheric particulate extracts. Using the optimized conditions, the analysis may be performed in less than a minute, with detection limits ranging from 22 fmols (16.7 µM) for levoglucosan to 336 fmols (258.7 µM) for galactosan. A comparison was made between GC/MS and microchip electrophoresis (FIG. 12) to demonstrate the capabilities of the device.

Example VII

Figure 13:
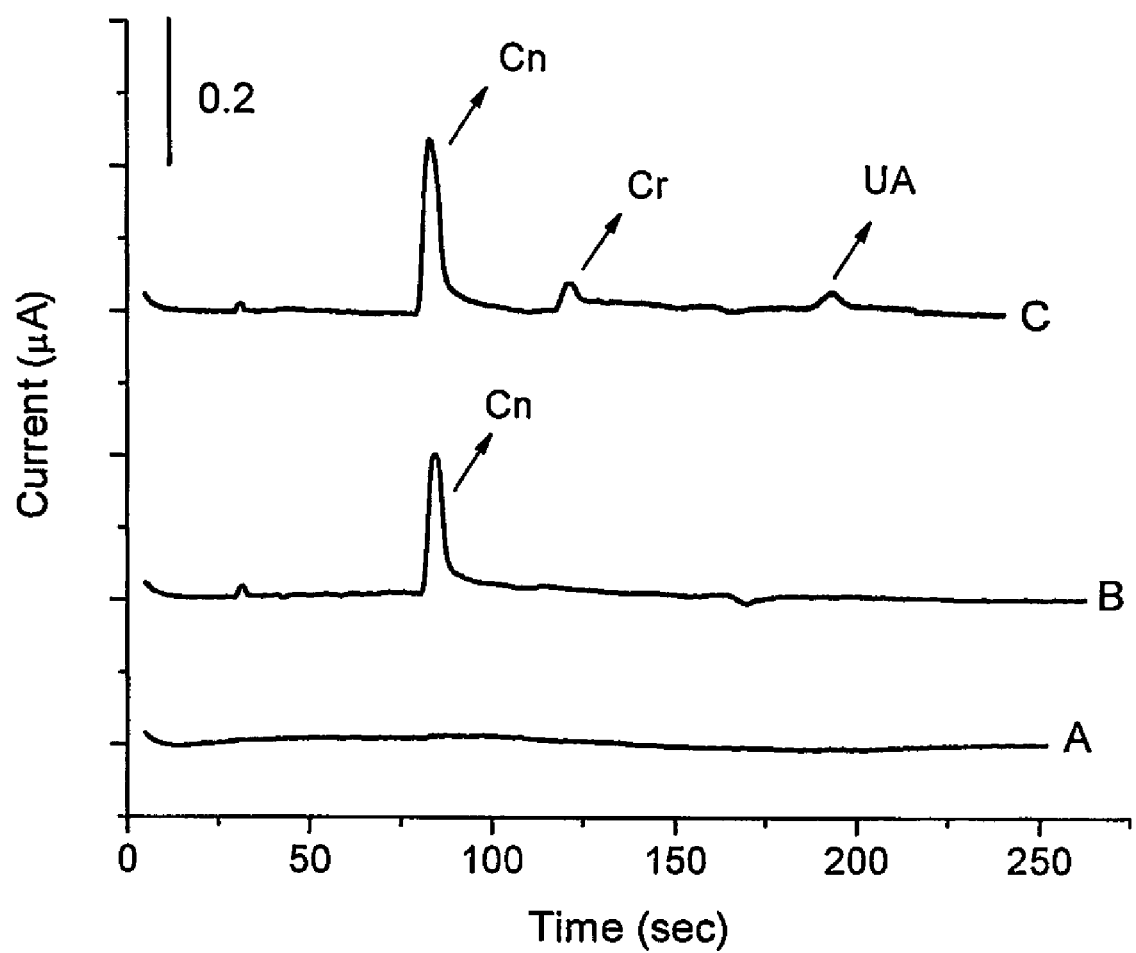
FIG. 13 shows electropherograms corresponding to a buffer injection (A), a 1/20 dilution of urine (B) and a 1/20 dilution of urine spiked with Cn, Cr and UA (C) for peak identification.

Direct Detection of Renal Function Markers Using Microchip CE with Pulsed Electrochemical Detection Creatinine, creatine, and uric acid are three important compounds that are measured in a variety of clinical assays, most notably for renal function. Traditional clinical assays for these compounds have focused on the use of enzymes or chemical reactions that may take up to 30 minutes to complete, only distinguish a single compound, are subject to interference, and are not portable. A number of separation methods have been applied to the analysis of creatinine, creatine, and uric acid to eliminate interferences and measure multiple compounds simultaneously. Capillary electrophoresis (CE) has been especially effective at providing fast, high-resolution separations from a variety of sample matrixes, including urine and serum. Traditional separation instrumentation cannot, however, be developed into point-of-care systems. Electrophoretic microchips according to the present invention have the potential to fill this important medical niche by integrating the separation power of capillary electrophoresis with devices that are small, portable, and have the speed of conventional sensors. The development of a microchip CE system for the direct detection of creatinine, creatine, and uric acid is discussed in the present example. The device uses pulsed amperometric detection (PAD) to detect the nitrogen-containing compounds as well as the easily oxidizable uric acid. Baseline separation of creatinine, creatine and uric acid was achieved using 30 mM borate buffer (pH=9.4) as the separation media in less than 200 seconds. Linear calibration curves were obtained with limits of detection of 80 µM, 250 µM and 270 µM for creatinine, creatine and uric acid respectively. Finally, analysis of a real urine sample is presented (FIG. 13) with validation of creatinine concentrations determined using a clinical assay kit based on the Jaffe reaction.

Example VIII

Figure 14A:
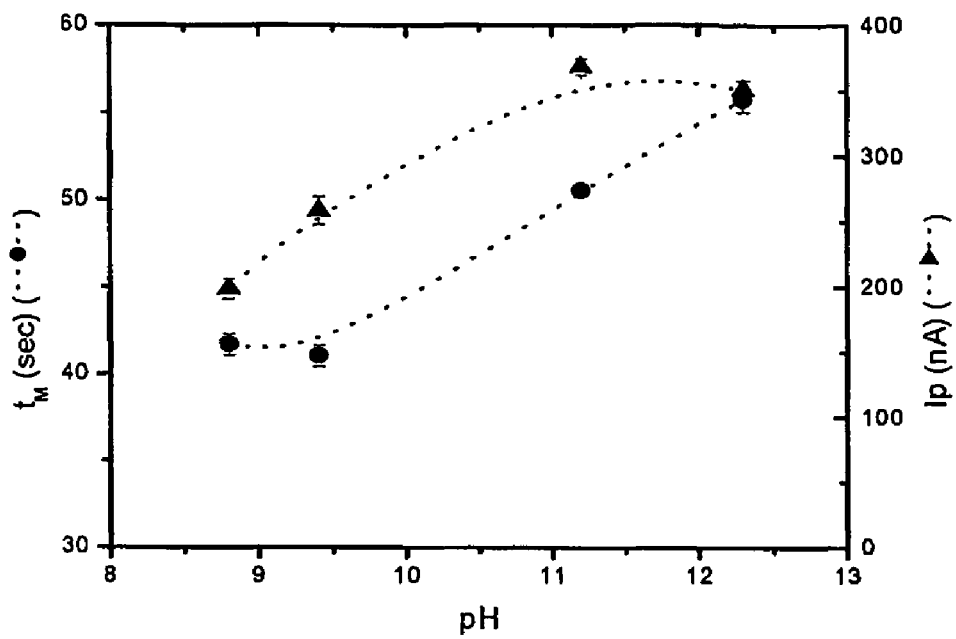
FIG. 14 illustrates (A) the effect of the pH of the running buffer on the migration time (--●--) and $I_p$ (--▲--) using pH=12.3 at the detection reservoir with the following conditions: GLU=8 mM, 10 mM borate with 2.4 mM SDS, detection potential=0.7V, 5 s injection; and (B) the effect of the pH of the detection buffer on the migration time (--●--) and $I_p$ (--▲--) using pH=9.4 as running buffer with the following conditions: GLU=8 mM, 10 mM borate with 2.4 mM SDS, detection potential=0.7V, 5 s injection.
Figure 14B:
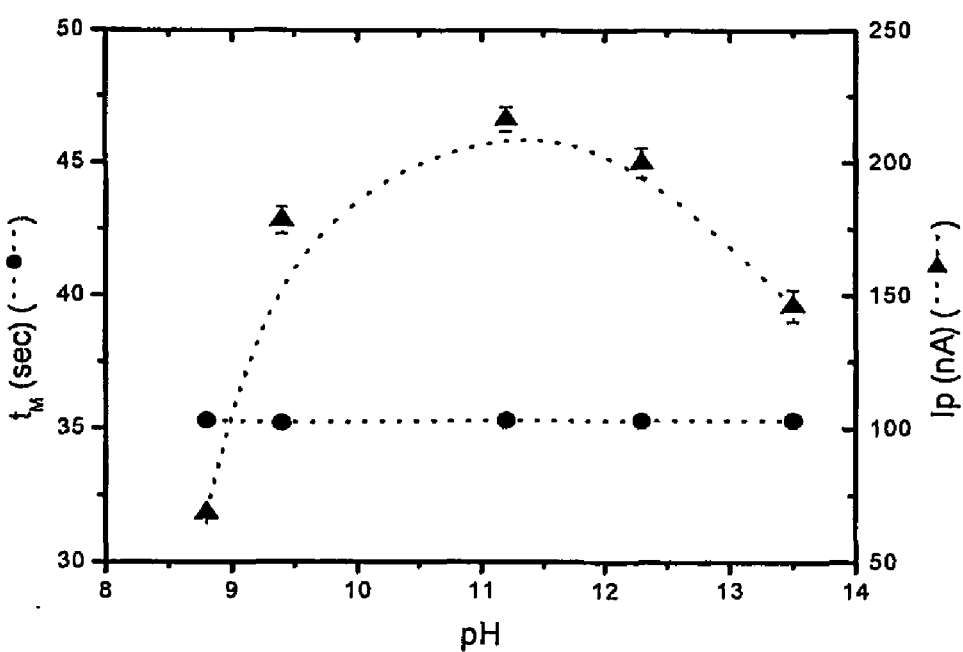
Figure 15:
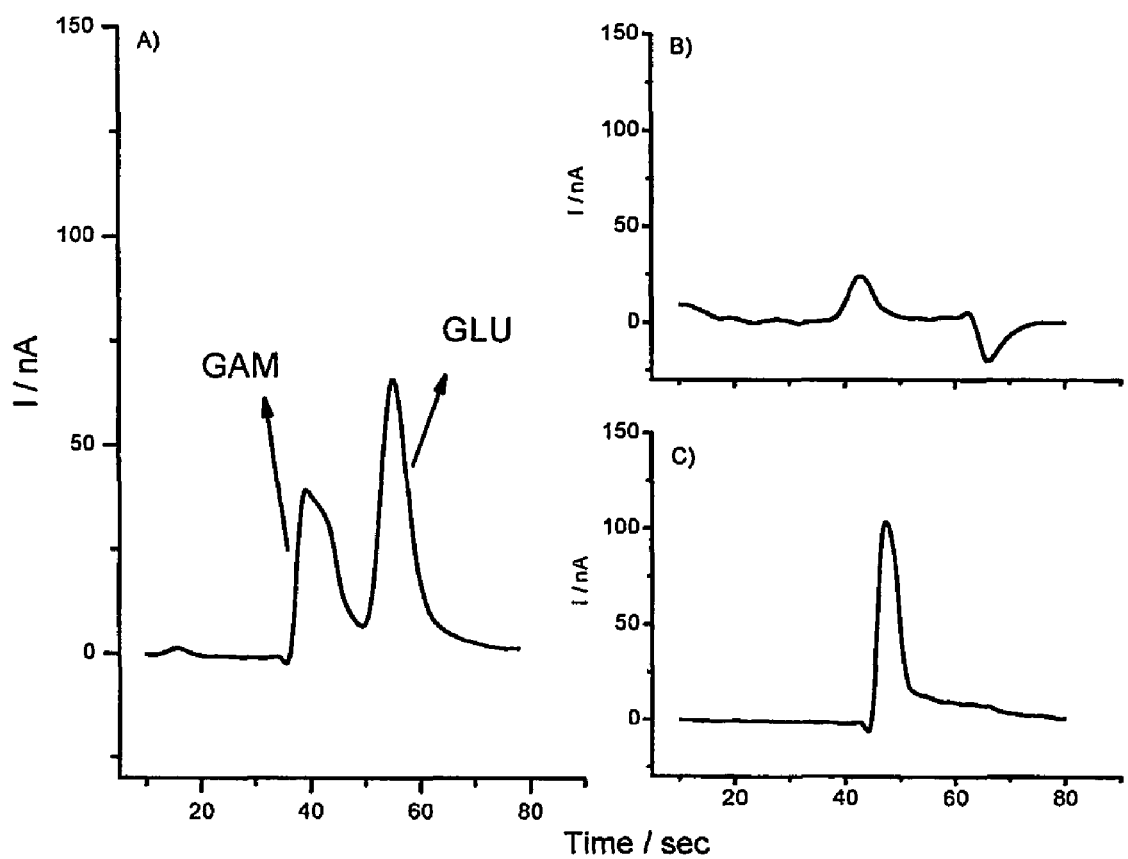
FIG. 15 shows A) an electropherogram of GLU and GAM obtained using 5 mM borate (pH=7.1)+2.4 mM SDS as the separation buffer and 5 mM borate (pH=11.1)+2.4 mM SDS as the detection buffer; B) an electropherogram of GLU and GAM obtained using 5 mM borate (pH=7.1)+2.4 mM SDS as the separation buffer and 5 mM borate (pH=7.1)+2.4 mM SDS as the detection buffer; and C) an electropherogram of GLU and GAM obtained using 5 mM borate (pH=11.1)+2.4 mM SDS as the separation buffer and 5 mM borate (pH=11.1)+2.4 mM SDS as the detection buffer.

Enhanced Determination of Glucose by Microchip Electrophoresis with Pulsed Amperometric Detection The present example describes a new analysis strategy for microchip capillary electrophoresis with pulsed amperometric detection and its application to the determination of glucose. The addition of sodium dodecyl sulfate to the mobile phase and detection reservoir stabilized flow rates and enhanced the detection signal for glucose (see FIGS. 14A and 14B). A higher pH (compared to the running buffer) was used at the waste reservoir in order to improve the detection performance while maintaining good separations. The present invention thus describes the use of post-column pH modification using microchip electrophoresis. Under optimum conditions, a linear relationship between the peak current and the concentration of glucose was found in the $10^{-2}$ to $10^{-5}$M, with a limit of detection of 1.2 µM. In addition, the separation of glucosamine and glucose was performed at pH=7.1 while the detection was performed at pH=11 to demonstrate the ability to use post column pH modification (FIG. 15). This approach is particularly useful when changes in pH improve the detection response and is analogous to the post-column modification performed in HPLC. Using the conditions above described, a 75-fold improvement in the LOD was achieved by the combination of both post column modification of pH and addition of SDS to the BGE.

Example IX

Figure 16:
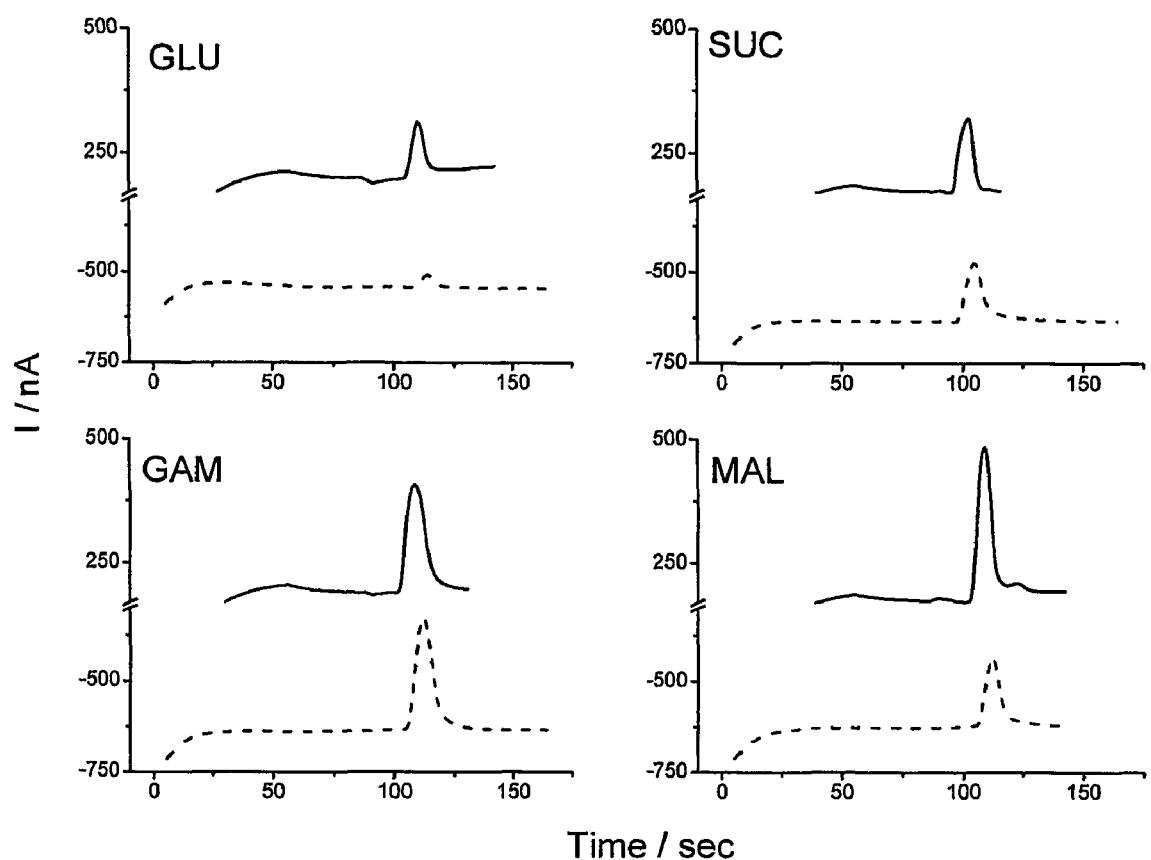
FIG. 16 shows a comparison of the electropherograms obtained by PAD and iPAD for 5.4 mM GLU, 2.8 mM SUC, 1.3 mM GAM and 1.9 mM MAL with the following conditions: 10 mM $Na_2B_4O_7$ pH=12.2+0.8 mM SDS.

Comparison of Pulsed Electrochemical Detection Modes Coupled with Microchip Capillary Electrophoresis There is a need to develop analytical methods that are capable of rapidly measuring small biological markers in the field of metabolomics. Among others, carbohydrates play an important role biologically, yet are traditionally hard to detect since they have no chromophore or fluorophore. In the present example, the application of integrated pulsed amperometric detection (iPAD) coupled with microchip electrophoresis to the analysis of glucose, mannose, sucrose, maltose, glucosamine, lactose, maltotriose and galactose is demonstrated. iPAD is an electrochemical detection mode that may be used for direct detection of carbohydrates, amines and sulfur containing compounds. The effect of different solutions parameters, including the buffer concentration, pH and the SDS concentration on separation and detection response was analyzed. In addition, a comparison study between PAD and iPAD was performed using a hexose (glucose), a modified hexose (glucosamine) and two disaccharides (sucrose) and (maltose) as model carbohydrates (FIG. 16).

Results show that both iPAD and PAD are affected in a similar manner by changes in solution conditions. For both detection methods, the highest electrochemical responses were obtained using lower electrolyte concentrations (4 mM), higher pH values (12.2) and a moderate level of SDS (0.8 mM). Using the described conditions, no further improvements in the separation efficiency were obtained with respect to previously reported results. However, if an increase in resolution is needed, the concentration of borate may be increased. Both PAD and iPAD responses are affected by a number of variables, but the effect on the relative response is similar. In general, iPAD requires a longer time for the waveform optimization step due to the larger number of variables involved. Nevertheless, it allows the detection of a variety of compounds and may improve the peak shape (height/width) with respect to PAD.

Thus, in the present invention as described above in the detailed description and examples, the construction of a device for pulsed amperometric detection has been described, and the capabilities of the microchip-CE-PAD system have been demonstrated. The separation and the direct detection of underivatized carbohydrates, amino acids and antibiotics were achieved by utilizing and optimizing the electric field, the electrolyte composition and the PAD parameters.

In certain embodiments and examples of the present invention, conditions were used such as +1000V as the separation potential, 10 mM borate buffer (pH=12.00) and 0.7V for the detection potential for carbohydrates, +1700V as the separation potential, 10 mM borate buffer (pH=9.45) and either 0.7V or 0.5V as the detection potential for amino acids and antibiotics respectively. The inclusion of an Au wire microelectrode was also demonstrated, showing very good stability and mass limits of detection in the fmol range. The present invention also allows the easy and fast positioning of an electrode at the end of a separation channel, increasing the reproducibility of chip-to-chip analysis. These specific examples are for illustration purposes and should be viewed as such. Thus, it should be appreciated that the parameters discussed in the present application may be adjusted or modified according to the teachings of the present application by one of ordinary skill in the art.

All documents, patents, journal articles and other materials cited in the present application are hereby incorporated by reference. Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A microchip comprising
a first layer and a second layer, said first layer comprising:
at least one main separation channel formed in a channel forming medium, said main separation channel containing microfluids when in operation;
electrodes in reservoirs at the ends of said main separation channel to drive electrophoretic separation;
at least one detecting channel containing a first conductive element for performing electrochemical detection, said detecting channel being formed in said channel forming medium within said first layer and adjoining said main separation channel, wherein said main separation channel and said detecting channel intersect; and
at least one reservoir containing a second conductive element for serving as a reference to said first conductive element, said reservoir being formed in said channel forming medium, said second layer being absent a conductive element, separation channel and detection channel.

2. The microchip of claim 1, wherein said detecting channel intersects said main separation channel at a point defined as an angle of approximately a 90°.

3. The microchip of claim 1, wherein said detecting channel intersects said main separation channel at a point defined as an angle of less than a 90°.

4. The microchip of claim 1, wherein said detecting channel intersects said main separation channel at a point defined as an angle of greater than a 90°.

5. The microchip of claim 1, wherein said detecting channel intersects said main separation channel at any an end point of said main channel.

6. The microchip of claim 1, wherein said channel forming medium comprises a polymeric material comprising poly (dimethylsiloxane).

7. The microchip of claim 1, wherein said channel forming medium comprises a polymeric material comprising poly (methylmethacrylate).

8. The microchip of claim 1, wherein at least one of aid conductive element and second conductive element comprises a gold wire.

9. The microchip of claim 1, wherein at least one of aid conductive element and second conductive element comprises a platinum wire.

10. The microchip of claim 1, wherein at least one of said first conductive element and said second conductive element comprises a palladium wire.

11. The microchip of claim 1, wherein at least one of said first conductive element and said second conductive element comprises a copper wire.

12. The microchip of claim 1, wherein at least one of said first conductive element and said second conductive element comprises a nickel wire.

13. The microchip of claim 1, wherein at least one of said first conductive element and said second conductive element comprises a nickel-alloy wire.

14. The microchip of claim 1, wherein at least one of said first conductive element and said second conductive element comprises a carbon fiber.

15. The microchip of claim 1, wherein said first conductive element and said second conductive element comprises a carbon paste.

16. The microchip of claim 1, wherein at least one detecting channel comprises a plurality of detecting channels.

17. A method of forming a microchip comprising: a first layer and a second layer, said first layer being prepared by
forming a main separation channel in a channel forming medium, said main separation channel having a reservoir at each end, each of said reservoirs containing an electrode to drive electrophoresis;
forming a detecting channel in a channel forming medium, wherein said detecting channel adjoins a main channel within said first layer;
placing a first conductive element in said detecting channel; and
placing a second conductive element in said reservoir or said detecting channel to thereby form said microchip, wherein said second layer is absent a conductive element, separation channel and detection channel.

18. The method of claim 17, further comprising sealing said first layer and said second layer with at least one sealing medium.

19. The method of claim 17, wherein said main separation channel, said detecting channel, and said reservoir are formed in said channel forming medium by molding.

20. The method of claim 17, wherein said detecting channel intersects said main channel within the first layer.

21. The method of claim 17, wherein said detecting channel intersects said main separation channel at approximately a 90° angle.

22. The method of claim 17, wherein said detecting channel intersects said main separation channel at less than a 90° angle.

23. The method of claim 17, wherein said detecting channel intersects said main separation channel at greater than a 90° angle.

24. The method of claim 17, wherein said detecting channel intersects said main separation channel at an end point of said channel.

25. The method of claim 17, wherein said channel forming medium comprises a polymeric material.

26. The method of claim 25 wherein said polymeric material comprises poly(methylmethacrylate) or poly(dimethylsiloxane).

27. The method of claim 17, wherein at least one first conductive element and second conductive element comprises a gold, platinum, palladium, copper, nickel, or nickel alloy wire, carbon fiber or carbon paste.

28. The method of claim 17, wherein at least one of said first conductive element and said second conductive element comprises a platinum wire.

29. The method of claim 17, wherein at least one of said first conductive element and said second conductive element comprises a palladium wire.

30. The method of claim 17, wherein at least one of said first conductive element and said second conductive element comprises a copper wire.

31. The method of claim 17, wherein at least one of said first conductive element and said second conductive element comprises a nickel wire.

32. The method of claim 17, wherein at least one of said first conductive element and said second conductive element comprises a nickel-alloy wire.

33. The method of claim 17, wherein at least one of said first conductive element and said second conductive element comprises a carbon fiber.

34. The method of claim 17, wherein at least one of said first conductive element and said second conductive element comprises carbon paste.

35. The method of claim 17, wherein said at least one detecting channel comprises a plurality of detecting channels.

36. A method of performing electrophoresis comprising:
attaching a first conductive element and a second conductive element to a microchip having at least one test microfluid thereon, wherein said microchip comprises:
a first layer and a second layer, said first layer comprising at least one main separation channel formed in a channel forming medium, said main channel containing at least one microfluid; and
at least one detecting channel containing said first conductive element for performing electrochemical detection, said detecting channel being formed within said first layer of said channel forming medium and adjoining said main separation channel; and at least one reservoir containing said second conductive element to provide a reference to said first conductive element, said second layer being absent a conductive element, separation channel and detection channel; and
applying electrochemical, continuous or pulsed amperometric detection to said microchip using said conductive elements,
wherein specimens within said microfluid migrate toward said first conductive element and electrodes in a reservoir at each end of said main channel drive electrophoretic transport in the microfluid, and wherein electrical contact with said first conductive element generates a measurable signal.

37. The method of claim 36, wherein said detecting channel intersects said main channel.

38. The method of claim 36, wherein said channel forming medium comprises a polymeric material.

39. The method of claim 36, wherein said channel forming medium comprises poly(methylmethacrylate) or poly(dimethylsiloxane).

40. The method of claim 36, wherein at least one first conductive element and second conductive element comprise gold, platinum, palladium, copper, nickel, nickel alloy, carbon fiber or carbon paste.

41. The method of claim 36, wherein at least one detecting channel comprises a plurality of detecting channels.

42. The method of claim 36, wherein said specimens comprises a carbohydrate, an amino acid, a protein, an antibiotic, levoglucosan, creatinine, creatine, uric acid, an amine, a thiol, an alcohol, or a mixture thereof.

43. The method of claim 36, wherein said continuous or pulsed amperometric detection provides an electrical potential across said microchip to provide separation and detection of at least one specimen in said microfluid.

44. The method of claim 43, wherein said electrical potential applied for separating the specimens contained in said microfluid comprises approximately +100V to approximately +5000V.

45. The method of claim 43, wherein said electrical potential applied for separating the specimens contained in said microfluid comprises approximately +0.4V to approximately +1.0V.

46. The method of claim 36, further comprising injecting said microfluid into a channel of said microchip at an electrical potential of approximately +100V, or approximately +500V.

47. The method of claim 46, wherein the injecting step is performed for between approximately 1 second and approximately 1 minute.

48. The method of claim 36, further comprising injecting said microfluid into a channel of said microchip at an electrical potential of approximately +160V.

49. The method of claim 36, further comprising injecting said microfluid into a channel of said microchip at an electrical potential of approximately +410V.

50. The method of claim 36, further providing, in combination with said at least one microfluid, an electrolyte solution.

51. The method of claim 50, wherein said electrolyte solution comprises borate.

52. The method of claim 50, wherein said electrolyte solution comprises a pH of approximately 7.1 to approximately 13 or a pH of approximately 9.45, or a pH of approximately 11, or a pH of approximately 12.

53. The method of claim 42 wherein the specimen comprises glycated hemoglobin.

54. The method of claim 42 wherein the specimen comprises hemocysteine.

55. The method of claim 42 wherein the specimen comprises uric acid.

* * * * *